(12) United States Patent
Yang et al.

(10) Patent No.: US 9,837,619 B2
(45) Date of Patent: Dec. 5, 2017

(54) DELAYED FLUORESCENCE COMPOUND, AND ORGANIC LIGHT EMITTING DIODE AND DISPLAY DEVICE USING THE SAME

(71) Applicant: LG Display Co., Ltd., Seoul (KR)

(72) Inventors: Joong-Hwan Yang, Gwangmyeong-si (KR); Kyung-Jin Yoon, Goyang-si (KR); Hyo-Jin Noh, Paju-si (KR); Dae-Wi Yoon, Paju-si (KR); In-Ae Shin, Paju-si (KR); Jun-Yun Kim, Goyang-si (KR)

(73) Assignee: LG Display Co., Ltd., Seoul (KR)

( * ) Notice: Subject to any disclaimer, the term of this patent is extended or adjusted under 35 U.S.C. 154(b) by 126 days.

(21) Appl. No.: 14/885,785

(22) Filed: Oct. 16, 2015

(65) Prior Publication Data

US 2016/0111660 A1    Apr. 21, 2016

(30) Foreign Application Priority Data

Oct. 17, 2014  (KR) .................. 10-2014-0140972
Oct. 17, 2014  (KR) .................. 10-2014-0140973
Sep. 15, 2015  (KR) .................. 10-2015-0130520
Sep. 16, 2015  (KR) .................. 10-2015-0130917

(51) Int. Cl.
*H01L 51/54* (2006.01)
*C09K 11/06* (2006.01)
(Continued)

(52) U.S. Cl.
CPC ........ *H01L 51/0072* (2013.01); *C07D 487/04* (2013.01); *C07D 487/06* (2013.01);
(Continued)

(58) Field of Classification Search
CPC ..... C09K 11/02; C09K 11/06; C09K 2211/00; C09K 2211/10; C09K 2211/1003; C09K 2211/1007; C09K 2211/1011; C09K 2211/1014; C09K 2211/1018; C09K 2211/1029; C09K 2211/1044; C09K 2211/1059; C09K 2211/1092; C07D 487/00; C07D 487/02; H01L 27/3258; H01L 51/0032; H01L 51/005; H01L 51/0059; H01L 51/0061; H01L 51/0067; H01L 51/0071; H01L 51/0072; H01L 51/0074; H01L 51/50; H01L 51/5004; H01L 51/5012; H01L 51/5016; H01L 51/5056; H01L 51/5072; H01L 51/5088; H01L 51/5092; H01L 51/5237; H01L 2251/552
(Continued)

(56) References Cited

U.S. PATENT DOCUMENTS

2012/0075273 A1* 3/2012 Abe ............... C07D 487/06
                                                    345/205
2013/0320839 A1* 12/2013 Watanabe ........ H01L 51/0072
                                                    313/504

* cited by examiner

*Primary Examiner* — Andrew K Bohaty
(74) *Attorney, Agent, or Firm* — Fenwick & West LLP

(57) ABSTRACT

Discussed is a delayed fluorescence compound including a first electron donor moiety of indolo-[3,2,1-j,k]carbazole; a second electron donor moiety selected from indolo-[3,2,1-j,k]carbazole, carbazole, or triphenylamine; and an electron acceptor moiety selected from dibenzothiophene sulfone or diphenyl sulfone, wherein the first and second electron donor moieties are combined to the electron acceptor moiety, and the electron acceptor moiety is combined to a third position or a sixth position of the first electron donor moiety.

19 Claims, 3 Drawing Sheets

(51) Int. Cl.
*H01L 51/00* (2006.01)
*C07D 487/04* (2006.01)
*C07D 487/06* (2006.01)
*H01L 51/52* (2006.01)
*H01L 51/50* (2006.01)

(52) U.S. Cl.
CPC .......... C09K 11/06 (2013.01); H01L 51/0059 (2013.01); H01L 51/0061 (2013.01); H01L 51/0074 (2013.01); H01L 51/5004 (2013.01); H01L 51/5237 (2013.01); *C09K 2211/1014* (2013.01); *C09K 2211/1029* (2013.01); *C09K 2211/1092* (2013.01); *H01L 51/5012* (2013.01); *H01L 51/5056* (2013.01); *H01L 51/5072* (2013.01); *H01L 51/5088* (2013.01); *H01L 51/5092* (2013.01)

(58) Field of Classification Search
USPC ....... 428/690, 691, 917, 411.4, 336; 427/58, 427/66; 313/500–512; 257/40, 88–104, 257/E51.001–E51.052; 252/301.16–301.35
See application file for complete search history.

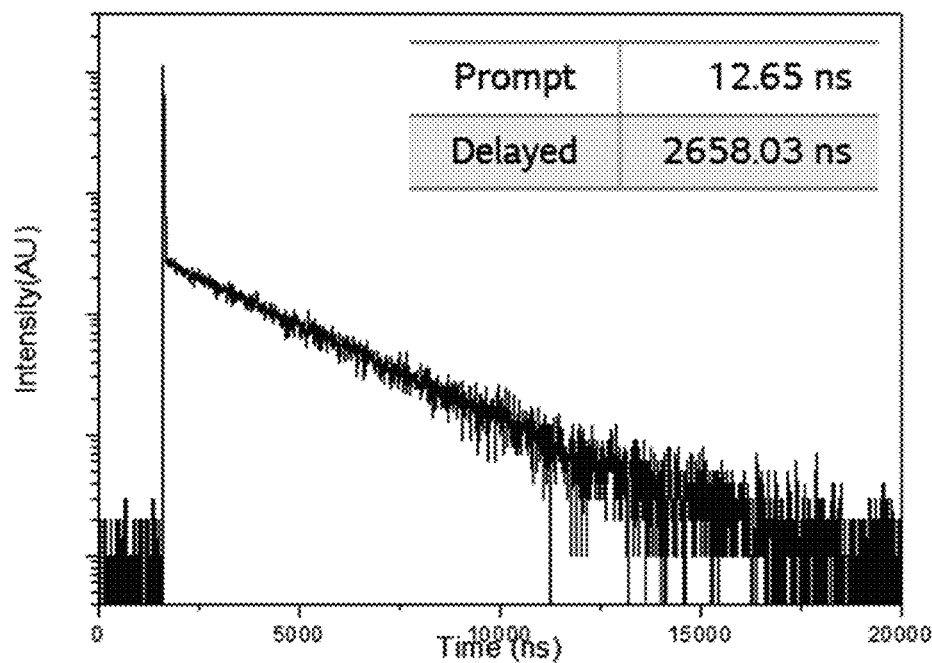
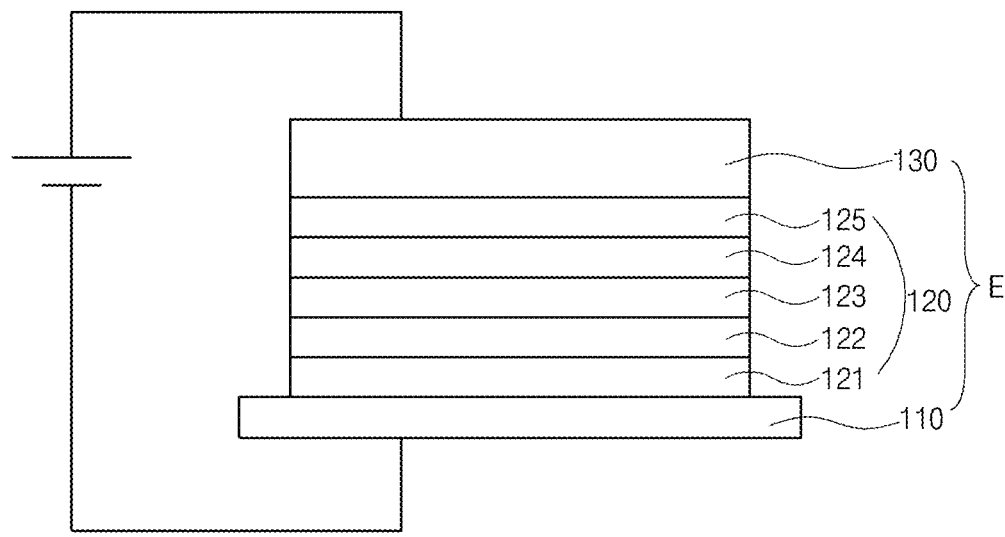

DELAYED FLUORESCENCE COMPOUND, AND ORGANIC LIGHT EMITTING DIODE AND DISPLAY DEVICE USING THE SAME

CROSS-REFERENCE TO RELATED APPLICATIONS

This application claims priority to and the benefit of Republic of Korea Patent Application No. 10-2014-0140972 filed on Oct. 17, 2014, Republic of Korea Patent Application No. 10-2014-0140973 filed on Oct. 17, 2014, Republic of Korea Patent Application No. 10-2015-0130520 filed on Sep. 15, 2015, and Republic of Korea Patent Application No. 10-2015-0130917 filed on Sep. 16, 2015, all of which are hereby incorporated by reference in their entirety.

BACKGROUND OF THE INVENTION

Field of the Invention

Embodiments of the invention relate to an organic light emitting diode (OLED) and more particularly to a delayed fluorescence compound having excellent emitting efficiency and an OLED and a display device using the delayed fluorescence compound.

Discussion of the Related Art

The requirements of the large-size display device have led to developments in flat panel display devices as an image displaying device. Among the flat panel display devices, the OLED has rapidly developed.

In the OLED, when the electron from a cathode, which serves as an electron-injecting electrode, and the hole from an anode, which serves as a hole-injecting electrode, are injected into an emitting material layer, the electron and the hole are combined and become extinct such that the light is emitted from the OLED. A flexible substrate, for example, a plastic substrate, can be used as a base substrate for the OLED, and the OLED has excellent characteristics of driving voltage, power consumption, and color purity.

The OLED includes a first electrode as an anode on a substrate, a second electrode as a cathode facing the first electrode, and an organic emitting layer therebetween.

To improve the emitting efficiency, the organic emitting layer may include a hole injection layer (HIL), a hole transporting layer (HTL), an emitting material layer (EML), an electron transporting layer (HTL), and an electron injection layer (EIL) sequentially stacked on the first electrode.

The hole is transferred into the EML from the first electrode through the HIL and the HTL, and the electron is transferred into the EML from the second electrode through the EIL and the ETL.

The electron and the hole are combined in the EML to generated excitons, and the excitons are transited from an excited state to a ground state such the light is emitted.

The External quantum efficiency of the emitting material for the EML can be expressed by the following equation:

$$\eta_{ext} = \eta_{int} \times \Gamma \times \Phi \times \eta_{out\text{-}coupling}$$

In the above equation, "$\eta_{int}$" is the internal quantum efficiency, "$\Gamma$" is the charge balance factor, "$\Phi$" is the radiative quantum efficiency, and "$\eta_{out\text{-}coupling}$" is the out-coupling efficiency.

The charge balance factor "$\Gamma$" means a balance between the hole and the electron when generating the exciton. Generally, assuming 1:1 matching of the hole and the electrode, the charge balance factor has a value of "1". The radiative quantum efficiency "$\Phi$" is a value regarding an effective emitting efficiency of the emitting material. In the host-dopant system, the radiative quantum efficiency depends on a fluorescent quantum efficiency of the dopant.

The internal quantum efficiency "$\eta_{int}$" is a ratio of the excitons generating the light to the excitons generated by the combination of the hole and the electron. In the fluorescent compound, a maximum value of the internal quantum efficiency is 0.25. When the hole and the electron are combined to generate the exciton, a ratio of the singlet excitons to the triplet excitons is 1:3 according to the spin structure. However, in the fluorescent compound, only the singlet excitons excluding the triplet excitons are engaged in the emission.

The out-coupling efficiency "$\eta_{out\text{-}coupling}$" is a ratio of the light emitted from the display device to the light emitted from the EML. When the isotropic compounds are deposited in a thermal evaporation method to form a thin film, the emitting materials are randomly oriented. In this instance, the out-coupling efficiency of the display device may be assumed as 0.2.

Accordingly, the maximum emitting efficiency of the OLED including the fluorescent compound as the emitting material is less than approximately 5%.

To overcome the disadvantage of the emitting efficiency of the fluorescent compound, the phosphorescent compound, where both the singlet excitons and the triplet excitons are engaged in the emission, has been developed for the OLED.

The red and green phosphorescent compound having a relatively high efficiency are introduced and developed. However, there is no blue phosphorescent compound meeting the requirements in emitting efficiency and reliability.

SUMMARY OF THE INVENTION

Accordingly, embodiments of the invention are directed to a delayed fluorescence compound and an OLED and a display device using the same that substantially obviate one or more of the problems due to limitations and disadvantages of the related art.

An object of the embodiment of the invention is to provide a delayed fluorescence compound having high emitting efficiency.

Another object of the embodiment of the invention is to provide an OLED and a display device having an improved emission efficiency.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the embodiments of the invention, as embodied and broadly described herein, an aspect of an embodiment of the invention provides a delayed fluorescence compound including a first electron donor moiety of indolo-[3,2,1-j,k]carbazole; a second electron donor moiety selected from indolo-[3,2,1-j,k]carbazole, carbazole or triphenylamine; and an electron acceptor moiety selected from dibenzothiophene sulfone or diphenyl sulfone, wherein the first and second electron donor moieties are combined to the electron acceptor moiety, and the electron acceptor moiety is combined to a third position or a sixth position of the first electron donor moiety.

In another aspect of the embodiment of the invention, provided is a delayed fluorescence compound of Formula 1:

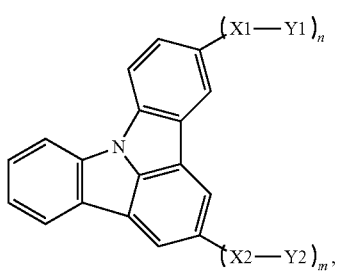

wherein one of m and n is 1, and the other one of m and n is 0, and wherein each of X1 and X2 is independently selected from Formula 2;

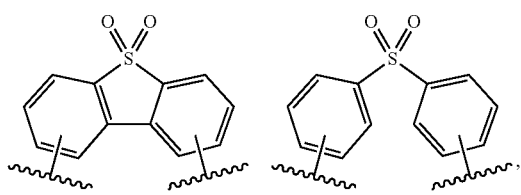

and each of Y1 and Y2 is independently selected from Formula 3:

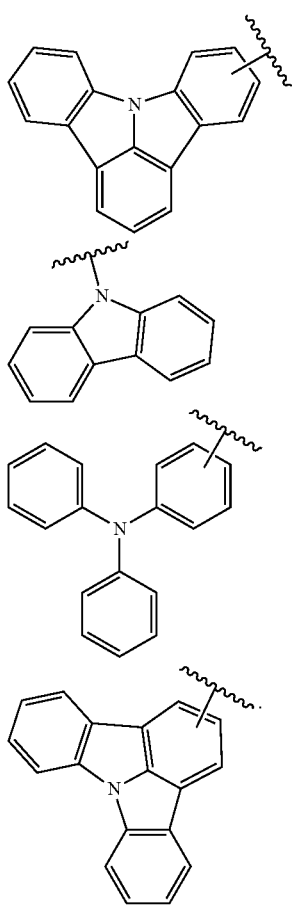

In another aspect of the embodiment of the invention provided is an organic light emitting diode including a first electrode; a second electrode facing the first electrode; and an organic emitting layer between the first and second electrodes and including a delayed fluorescence compound, wherein the delayed fluorescence compound includes a first electron donor moiety of indolo-[3,2,1-j,k]carbazole, a second electron donor moiety selected from indolo-[3,2,1-j,k]carbazole, carbazole or triphenylamine, and an electron acceptor moiety selected from dibenzothiophene sulfone or diphenyl sulfone, wherein the first and second electron donor moieties are combined to the electron acceptor moiety, and the electron acceptor moiety is combined to a third position or a sixth position of the first electron donor moiety.

In another aspect of the embodiment of the invention provided is an organic light emitting diode including a first electrode; a second electrode facing the first electrode; and an organic emitting layer between the first and second electrodes and including a delayed fluorescence compound of Formula 1:

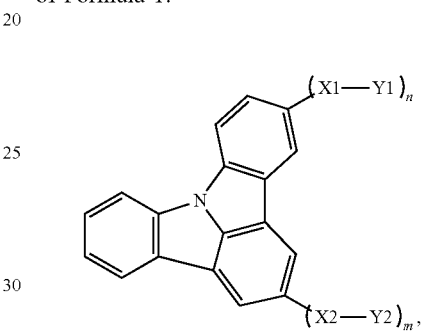

wherein one of m and n is 1, and the other one of m and n is 0, and wherein each of X1 and X2 is independently selected from Formula 2:

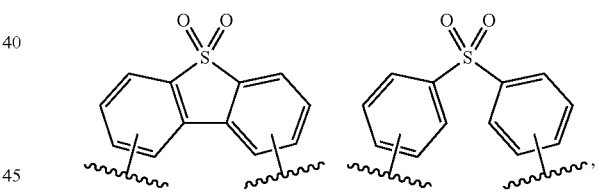

and each of Y1 and Y2 is independently selected from Formula 3:

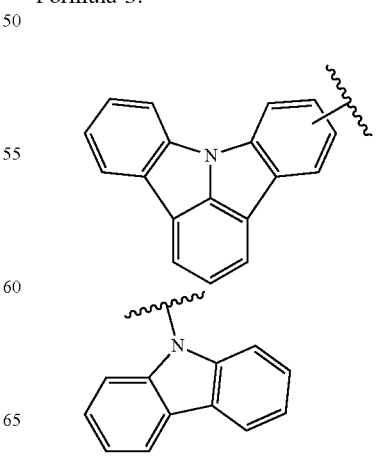

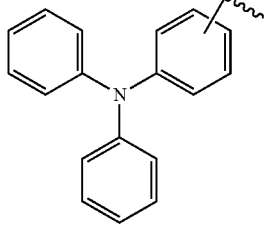

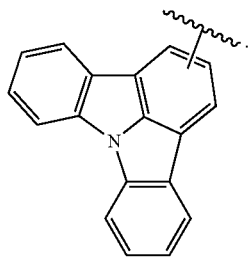

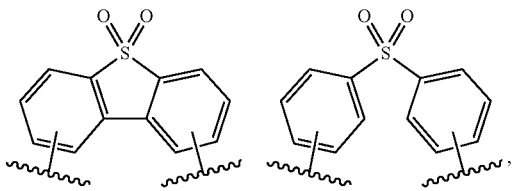

and each of Y1 and Y2 is independently selected from Formula 3:

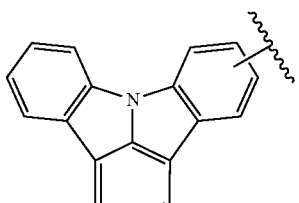

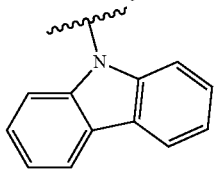

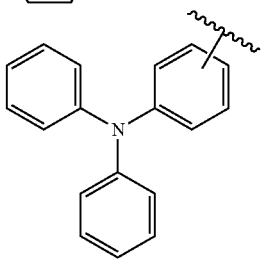

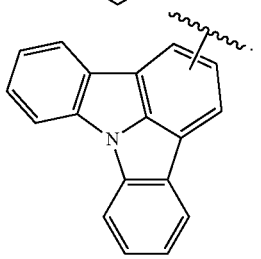

In another aspect of the embodiment of the invention provided is a display device including a substrate; an organic light emitting diode on the substrate and including a first electrode, a second electrode facing the first electrode and an organic emitting layer between the first and second electrodes and including a delayed fluorescence compound; an encapsulation film on the organic light emitting diode; and a cover window on the encapsulation film, wherein the delayed fluorescence compound includes a first electron donor moiety of indolo-[3,2,1-j,k]carbazole, a second electron donor moiety selected from indolo-[3,2,1-j,k]carbazole, carbazole or triphenylamine, and an electron acceptor moiety selected from dibenzothiophene sulfone or diphenyl sulfone, wherein the first and second electron donor moieties are combined to the electron acceptor moiety, and the electron acceptor moiety is combined to a third position or a sixth position of the first electron donor moiety.

In another aspect of the embodiment of the invention provided is a display device including a substrate; an organic light emitting diode on the substrate and including a first electrode, a second electrode facing the first electrode and an organic emitting layer between the first and second electrodes and including a delayed fluorescence compound of Formula 1:

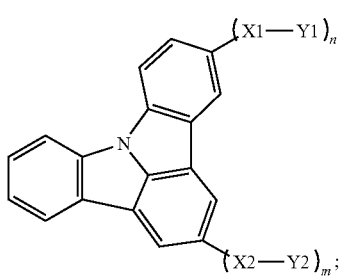

an encapsulation film on the organic light emitting diode; and a cover window on the encapsulation film, wherein one of m and n is 1, and the other one of m and n is 0, and wherein each of X1 and X2 is independently selected from Formula 2:

It is to be understood that both the foregoing general description and the following detailed description are by example and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

FIGS. 2A to 2D respectively show distribution of highest occupied molecular orbital (HOMO) and lowest unoccupied molecular orbital (LUMO) of compound 1 of the present invention.

FIG. 3 is a schematic cross-sectional view of an OLED according to the invention.

DETAILED DESCRIPTION OF THE EMBODIMENTS

Figure 1:
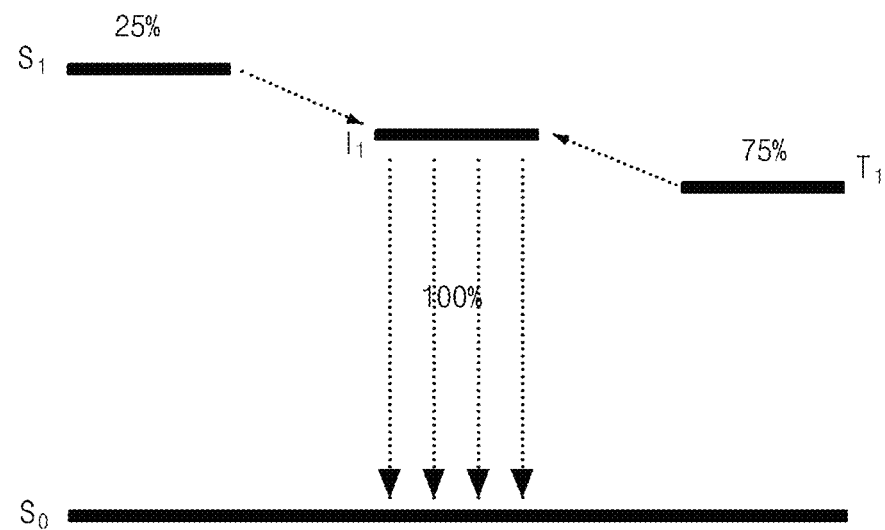
FIG. 1 is a view illustrating an emission mechanism of a delayed fluorescence compound according to the present invention.
Figure 2A:
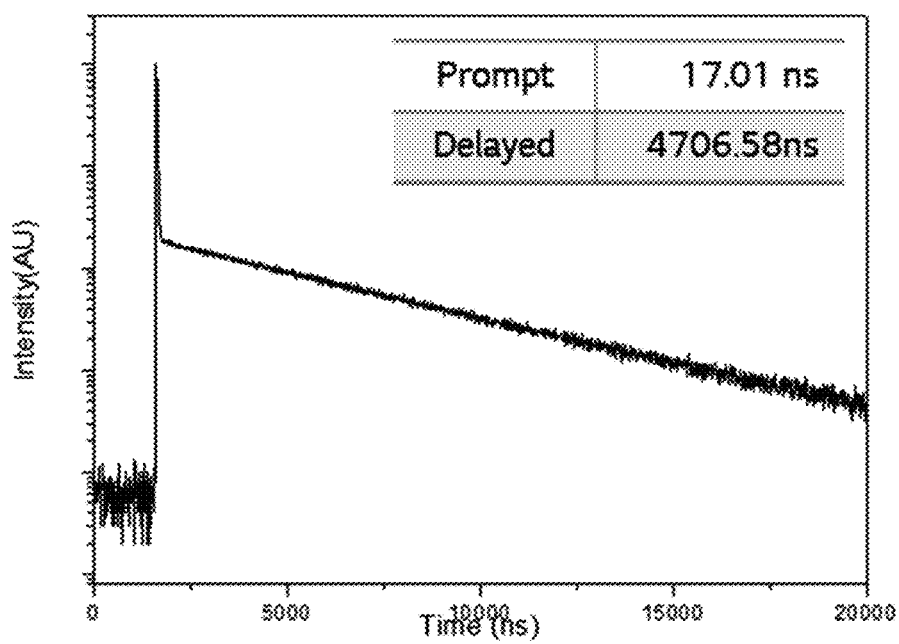
Figure 2B:
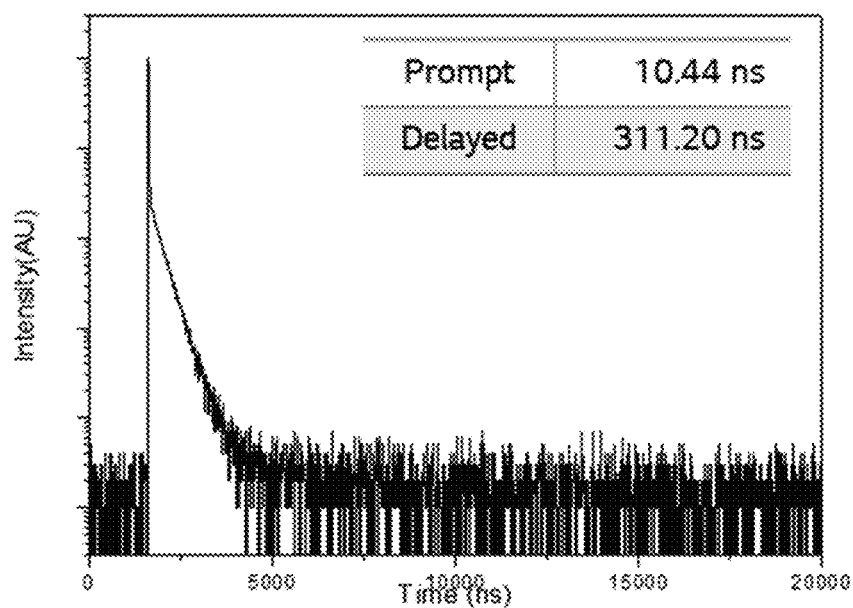
Figure 2C:
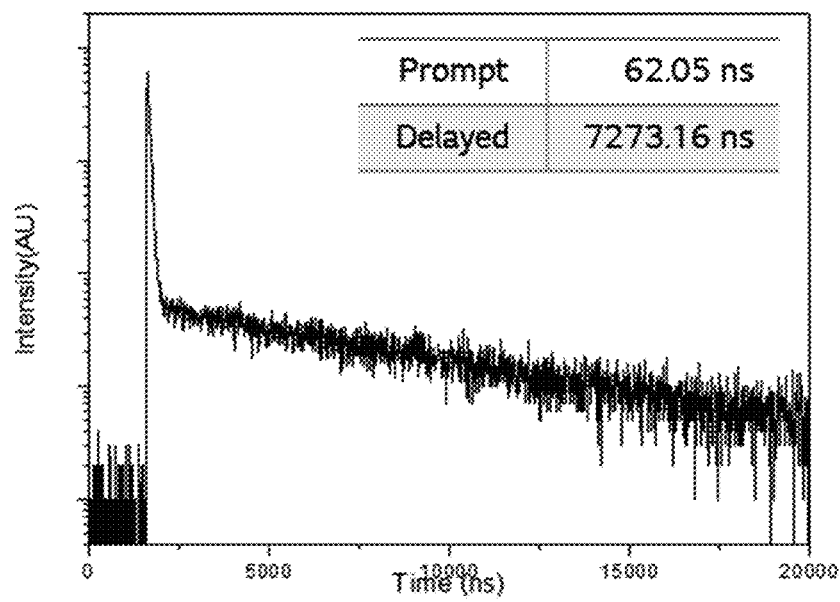

The meanings of terms described in the present specification should be understood as follows.

The singular forms should be understood as including the plural forms as well unless the context clearly indicates otherwise. The terms "first", "second", and the like are used to discriminate any one element from other elements and the scope of the present invention is not intended to be limited by these terms. The terms "comprises" "includes" and the like should be understood as not precluding the presence or addition of one or more other features, integers, steps, operations, elements, components, or combinations thereof. The term "at least one" should be understood as including all combinations that may be suggested from one or more associated items. For example, the meanings of "at least one selected from a first item, a second item, and a third item" includes not only each of the first item, the second item, and the third item, but also all combinations of these items that may be suggested from two or more ones of the first item, the second item, and the third item. In addition, when any one element is referred to as being "on" another element, it can be directly on the upper surface of the other element or a third intervening element may also be present.

Reference will now be made in detail to example embodiments, examples of which are illustrated in the accompanying drawings.

A delayed fluorescence compound of the present invention has a structure in that a first electron donor moiety of indolo-[3,2,1-j,k]carbazole and a second electron donor moiety are respectively combined (or linked) to an electron acceptor moiety and the electron acceptor moiety is combined to a third or sixth positions of the first electron donor moiety. The delayed fluorescent compound of the present invention has Formula 1 of following. [Formula 1]

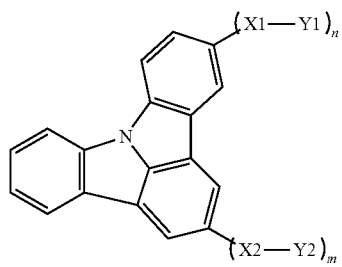

In the Formula 1, one of "m" and "n" is 1, and the other one of "m" and "n" is 0 (zero). Namely, the delayed fluorescent compound in the Formula 1 may have Formula 2-1 or Formula 2-2 of the following:

[Formula 2-1]

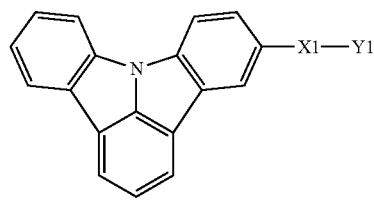

[Formula 2-2]

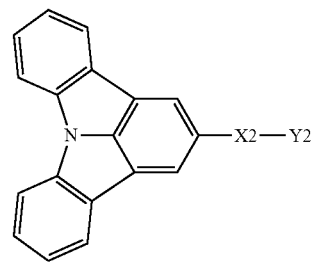

In other words, as shown in the Formula 2-1, the delayed fluorescence compound of the present invention may have a structure in that a first electron donor moiety of indolo-[3,2,1-j,k]carbazole and a second electron donor moiety are respectively combined (or linked) to an electron acceptor moiety and the electron acceptor moiety is combined to a third position of the first electron donor moiety.

Alternatively, as shown in the Formula 2-2, the delayed fluorescence compound of the present invention may have a structure in that a first electron donor moiety of indolo-[3,2,1-j,k]carbazole and a second electron donor moiety are respectively combined (or linked) to an electron acceptor moiety and the electron acceptor moiety is combined to a sixth position of the first electron donor moiety.

In the Formulas 1, 2-1 and 2-2, each of Y1 and Y2 as the second electron donor moiety is independently selected from indolo-[3,2,1-j,k]carbazole, carbazole or triphenylamine. The first and second electron donor moieties are same or different. For example, each of Y1 and Y2 as the second electron donor moiety is independently selected from materials in Formula 3 of following:

[Formula 3]

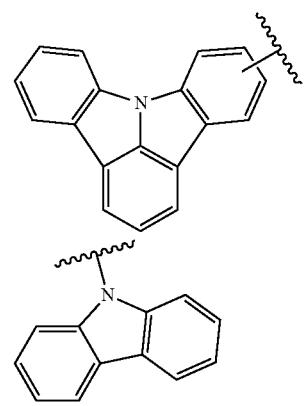

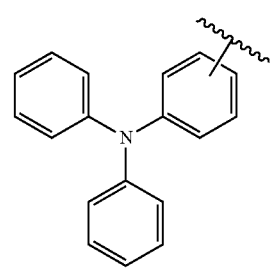

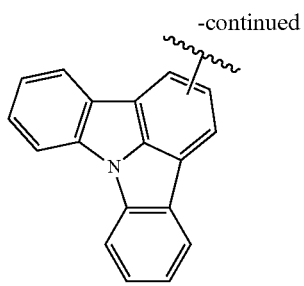

In the Formulas 1, 2-1 and 2-2, each of X1 and X2 as the electron acceptor moiety is independently selected from dibenzothiophene sulfone or diphenyl sulfone. For example, each of X1 and X2 as the second electron acceptor moiety is independently selected from materials in Formula 4 of following:

[Formula 4]

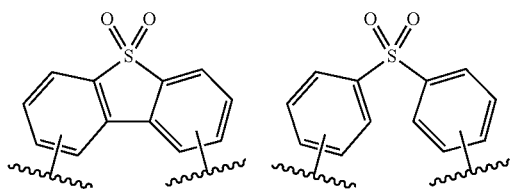

Since the delayed fluorescence compound includes the first and second electron donor moieties and the electron acceptor moiety, the charge transfer is easily generated in the molecule and the emitting efficiency is improved. In addition, the dipole from the first and second electron donor moieties to the electron acceptor moiety is generated such that the dipole moment in the molecule is increased. As a result, the emitting efficiency is further improved.

Moreover, in the delayed fluorescent compound of the present invention, the excitons in the triplet state are engaged in the emission such that the emitting efficiency of the delayed fluorescent compound is increased.

Further, since indolo-[3,2,1-j,k]carbazole, which has high triplet energy and excellent hole property, is used for the first electron donor moiety and optionally for the second electron donor moiety, the increase of the emitting efficiency is further increased. (HOMO: −5.56 eV, LUMO: −1.25 eV, $E_T$=3.04 eV)

The delayed fluorescence compound of the present invention has a rigid structure due to indolo-[3,2,1-j,k]carbazole such that the vibration in the molecule is decreased. As a result, the color shift problem is decreased, and the color purity is improved. In addition, since the delayed fluorescence compound of the present invention has large molecular weight, the thermal stability is increased.

In the delayed fluorescence compound of the present invention, the first and second electron donor moieties and the electron acceptor moiety are combined or linked in the molecule such that an overlap between highest occupied molecular orbital (HOMO) and lowest unoccupied molecular orbital (LUMO) is reduced. As a result, a field activated complex is generated, and the emitting efficiency of the delayed fluorescence compound is improved.

Referring to FIG. 1, which is a view illustrating an emission mechanism of a delayed fluorescence compound according to the present invention, in the delayed fluorescence compound of the present invention, the triplet excitons as well as the singlet excitons are engaged in the emission such that the emitting efficiency is improved.

Namely, the triplet exciton is activated by a field, and the triplet exciton and the singlet exciton are transferred into an intermediated state "$I_1$" and transited into a ground state "So" to emit light. In other words, the singlet state "$S_1$" and the triplet state "$T_1$" are transited into the intermediated state "$I_1$" ($S_1 \rightarrow I_1 \leftarrow T_1$), and the singlet exciton and the triplet exciton in the intermediated state "$I_1$" are engaged in the emission such that the emitting efficiency is improved. The compound having the above emission mechanism may be referred to as a field activated delayed fluorescence (FADF) compound.

In the related art fluorescence compound, since the HOMO and the LUMO are dispersed throughout an entirety of the molecule, the interconversion of the HOMO and the LUMO is impossible. (Selection Rule)

However, in the FADF compound, since the overlap between the HOMO and the LUMO in the molecule is relatively small, the interaction between the HOMO and the LUMO is small. Accordingly, changes of the spin state of one electron do not affect other electrons, and a new charge transfer band, which does not comply with the Selection Rule, is generated.

Moreover, since the electron donor moiety and the electron acceptor moiety is spatially spaced apart from each other in the molecule, the dipole moment is generated in a polarized state. In the polarized state dipole moment, the interaction between the HOMO and the LUMO is further reduced such that the emission mechanism does not comply with the Selection Rule. Accordingly, in the FADF compound, the transition from the triplet state "$T_1$" and the singlet state "$S_1$" into the intermediated state "$I_1$" can be generated such that the triplet exciton can be engaged in the emission.

When the OLED is driven, the intersystem transition (intersystem crossing) from 25% singlet state "$S_1$" excitons and 75% triplet state "$T_1$" excitons to the intermediated state "$I_1$" is generated, and the singlet and triplet excitons in the intermediated state "$I_1$" are transited into the ground state to emit the light. As a result, the FADF compound has the theoretic quantum efficiency of 100%.

For example, the delayed fluorescence compound in the Formula 1 may be one of compounds in Formula 5. (Compounds 1 to 12 in order.)

[Formula 5]

1

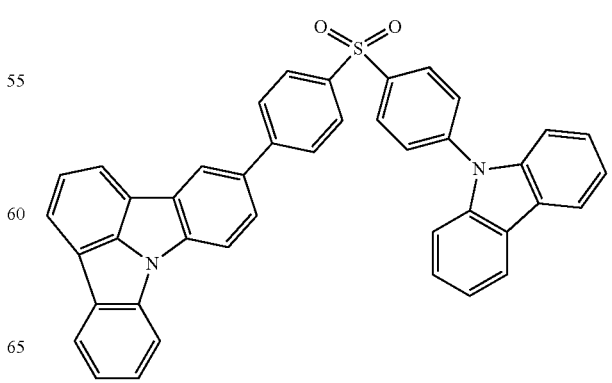

-continued
2
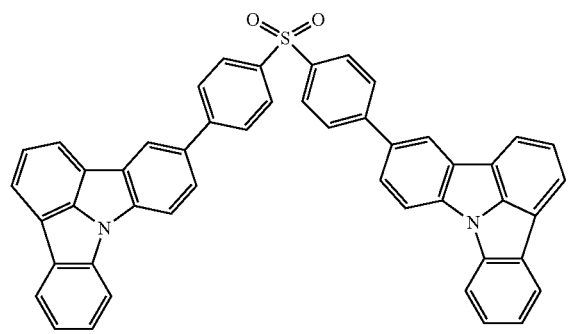
6
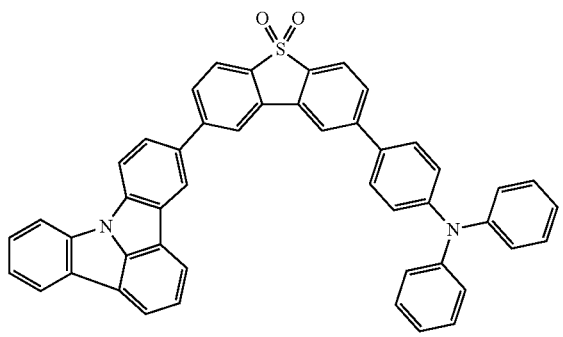
3
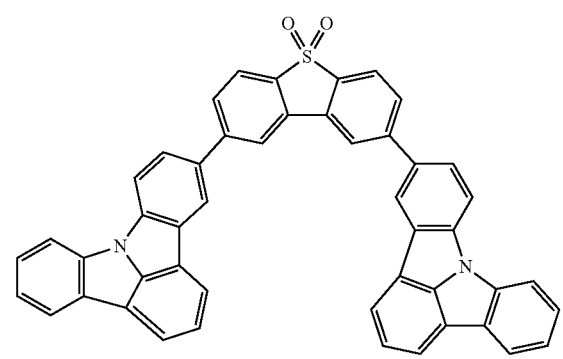
7
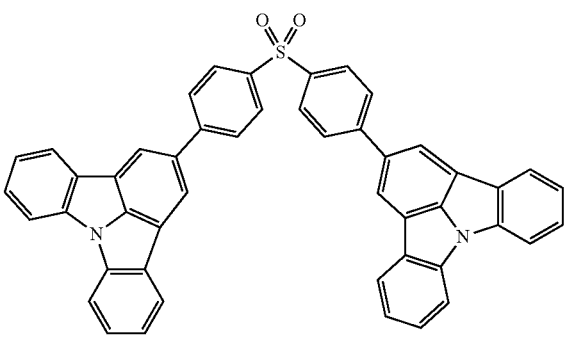
4
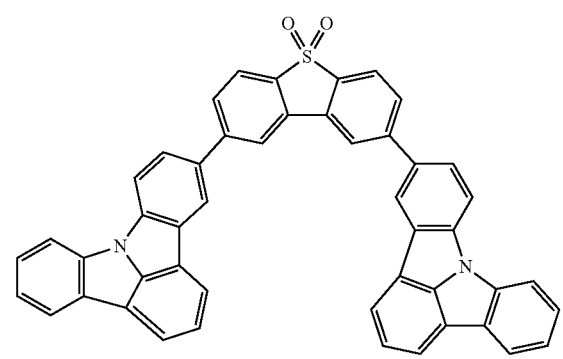
8
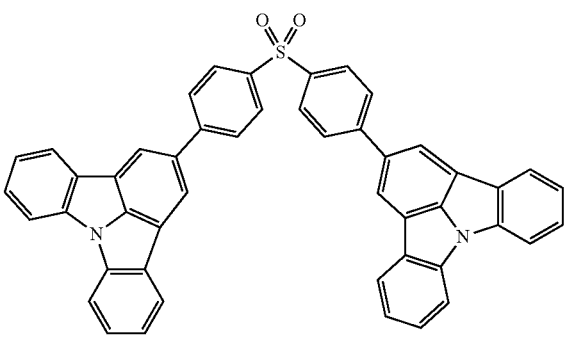
5
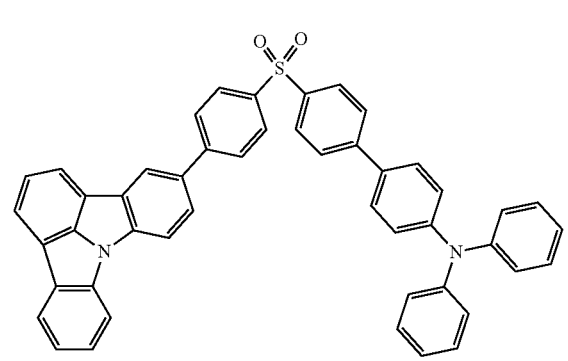
9
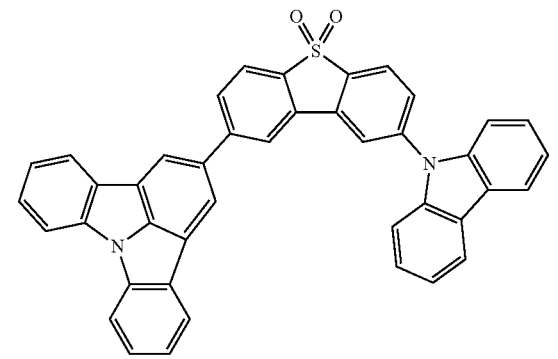

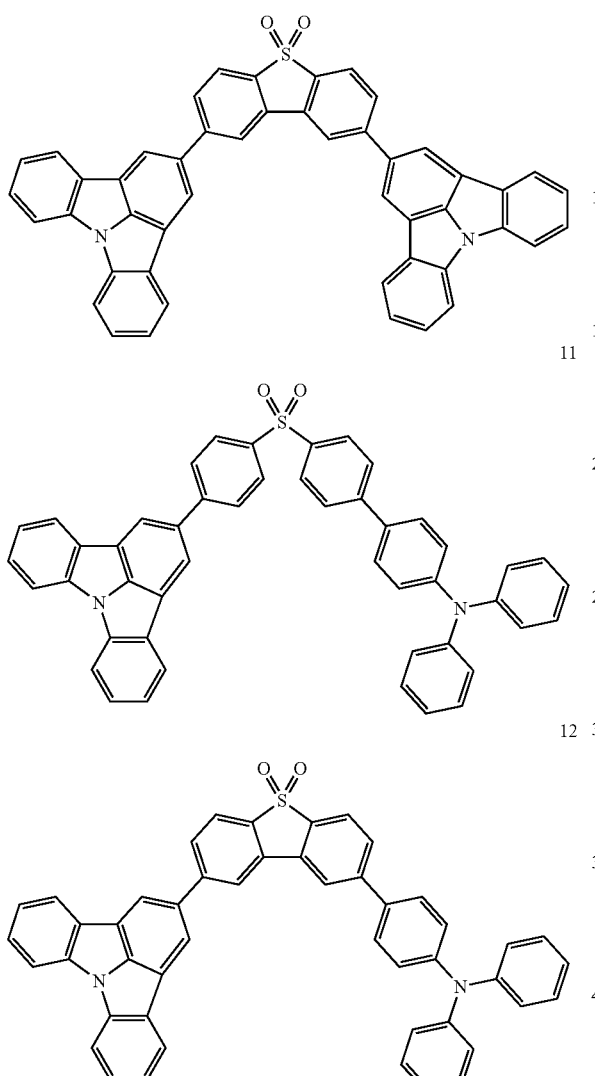

The HOMO, the LUMO and the energy band gap of the compounds 1 to 12 are listed in Table 1.

TABLE 1

|  | HOMO (eV) | LUMO (eV) | Band gap |
|---|---|---|---|
| Compound 1 | −5.58 | −1.67 | 3.91 |
| Compound 2 | −5.65 | −1.62 | 4.03 |
| Compound 3 | −5.94 | −1.96 | 3.98 |
| Compound 4 | −5.70 | −1.83 | 3.87 |
| Compound 5 | −5.12 | −1.59 | 3.53 |
| Compound 6 | −5.17 | −1.80 | 3.37 |
| Compound 7 | −5.68 | −1.52 | 4.16 |
| Compound 8 | −5.67 | −1.59 | 4.08 |
| Compound 9 | −5.62 | −1.91 | 3.71 |
| Compound 10 | −5.70 | −1.73 | 3.97 |
| Compound 11 | −5.10 | −1.51 | 3.59 |
| Compound 12 | −5.16 | −1.74 | 3.42 |

As shown in Table 1, the delayed fluorescence compound of the present invention has a large energy band gap such that the emitting efficiency of an OLED or a display device including the compound may be increased.

Synthesis

1. Synthesis of Compound 1
(1) Compound C

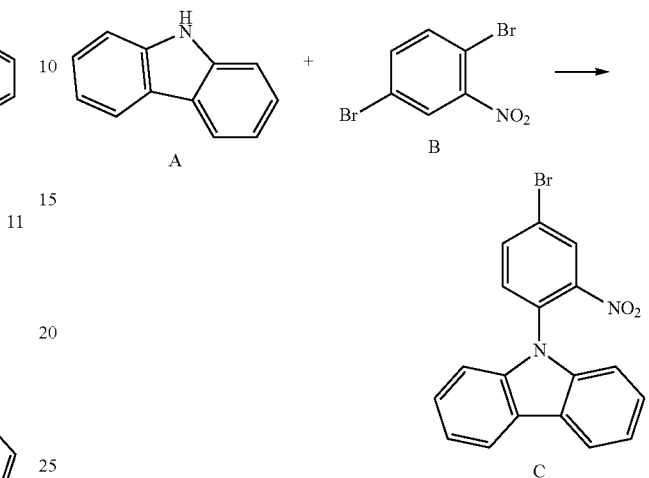

[Reaction Formula 1-1]

In the $N_2$ gas purging system, compound A, compound B (2 equivalent), potassium carbonate (2 equivalent), and copper (Cu) were put into diethylene glycol, and the mixture was stirred. After stirring for about 1 hour under a temperature of 240° C., the reaction was completed. The mixture was extracted by boiled acetone to remove the organic solvent. The resultant was put into the diluted hydrochloric acid solution. After washing by DI water, the resultant was re-crystallized by using acetone and methanol such that compound C was obtained.

(2) Compound D

[Reaction Formula 1-2]

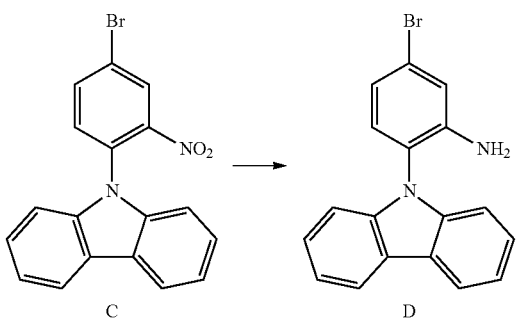

In the $N_2$ gas purging system, compound C was put into acetic acid, and the mixture was stirred under a temperature of 70° C. Activated zinc, which was activated with diluted hydrochloric acid, was added, and the mixture was refluxed for 1 hour after the color of the mixture was changed. After completion of the reflux, the mixture was cooled in room temperature, and DI water was added to obtain solids. The solids were filtered to remove zinc, and the residuals were put into acetic acid. Diluted hydrochloric acid by DI water (hydrochloric acid:DI water=1:10 (vol. %)) of excess amount was added into the mixture to obtain solids. The solids were washed by DI water such that compound D was obtained.

(3) Compound E

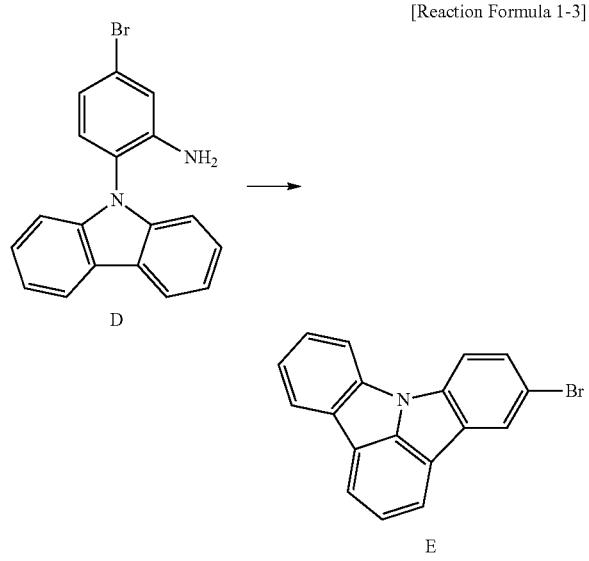

[Reaction Formula 1-3]

In the ice bath, compound D was put into acetic acid, and sulfuric acid was added and stirred. Sodium nitride (1.1 equivalent) was dissolved in DI water, and the solution was slowly added into the flask including the compound D for 15 minutes and was additionally stirred for 10 minutes. The flask was transferred into the oil bath, and the mixture was reacted for 20 minutes under a temperature of 130° C. After completion of the reaction, the mixture was cooled in room temperature, and DI water was put into the resultant to obtain the precipitates. The precipitates was filtered and washed by methanol. The filtered precipitate was columned and re-crystallized by using dichloromethane and methanol such that compound E was obtained.

(4) Compound F

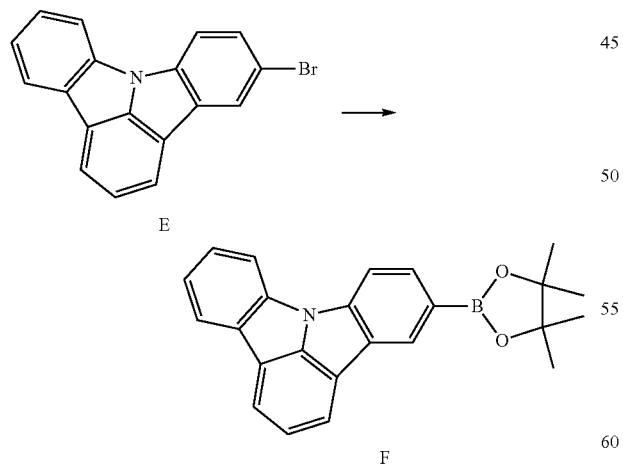

[Reaction Formula 1-4]

In the $N_2$ gas purging system, compound E, bis(pinacolate)diboron (1.2 equivalent), [1,1-bis(diphenylphosphineo)ferrocene]palladium(II), dichloride dichloromethane, 1,1-bis(diphenylphosphino)ferrocene and potassium acetate were put into the mixed solvent of 1,4-dioxane and toluene (1:1) in the flask, where the light was blocked out, and stirred. After the bubbles were disappeared, the mixture was stirred for 17 hours under a temperature of 120° C. in the oil bath. After completion of the reaction, the mixture was cooled in room temperature, and the solvent was removed. The resultant was washed by dichloromethane and refined such that compound F was obtained.

(5) Compound H

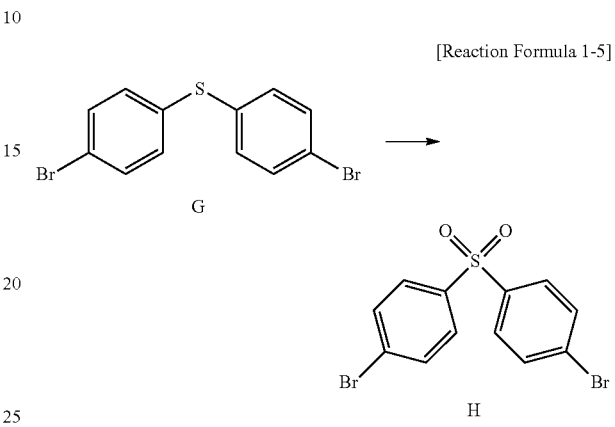

[Reaction Formula 1-5]

In the $N_2$ gas purging system, compound G was put into acetic acid and was stirred. 30% hydrogen peroxide was excessively added. The mixture was refluxed for 8 hours under a temperature of 110° C., and the reaction was completed. The mixture was cooled in room temperature, and water was added to be precipitate. The mixture was stirred for about 30 minutes, and the precipitate was filtered. The resultant was washed by water such that compound H was obtained.

(6) Compound I

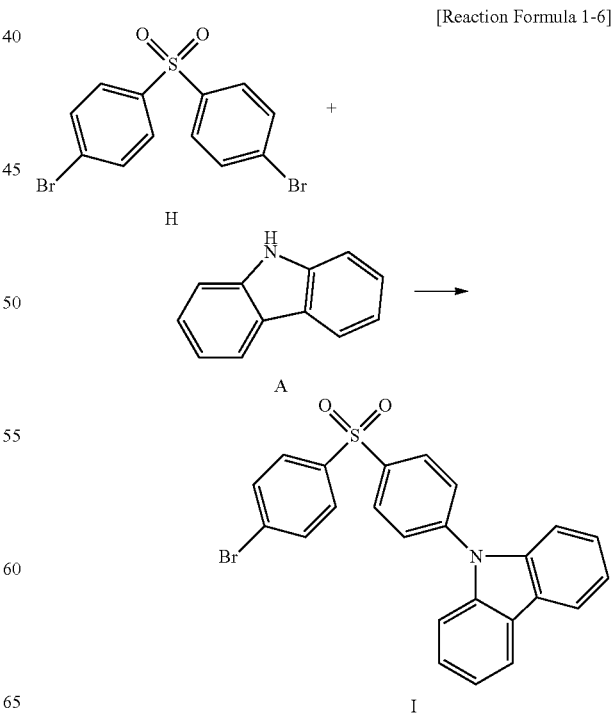

[Reaction Formula 1-6]

In the N₂ gas purging system, compound A (1 equivalent) was dissolved in 1,4-dioxane, and CuI and K₃PO₄ were added. Compound H (1.1 equivalent) and trans-1,2-diaminocyclohexane were added into the flask including the compound A. The mixture was stirred and refluxed for 24 hours under a temperature of 110° C. After completion of the reaction, the mixture, which was cooled in room temperature, was extracted by using water and ethyl acetate. The resultant was columned by using the solvent of ethyl acetate and hexane such that compound I was obtained.

(7) Compound 1

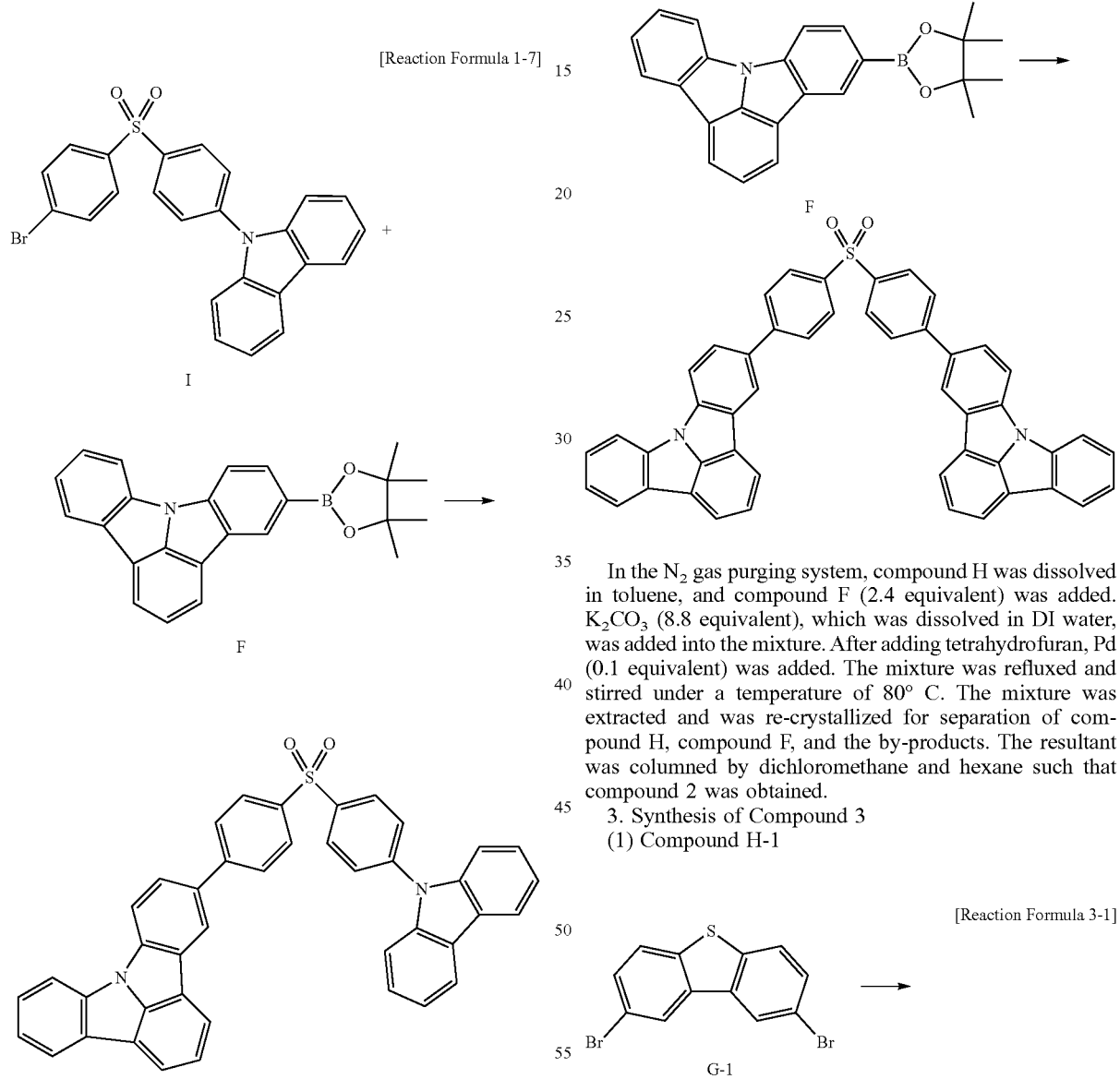

In the N₂ gas purging system, compound I was dissolved in toluene, and compound F (1.2 equivalent) was added. K₂CO₃ (4.4 equivalent), which was dissolved in DI water, was added into the mixture. After adding tetrahydrofuran, Pd (0.05 equivalent) was added. The mixture was refluxed and stirred under a temperature of 80° C. The mixture was extracted and was re-crystallized for separation of compound I, compound F, and the by-products. The resultant was columned by dichloromethane and hexane such that compound 1 was obtained.

2. Synthesis of Compound 2

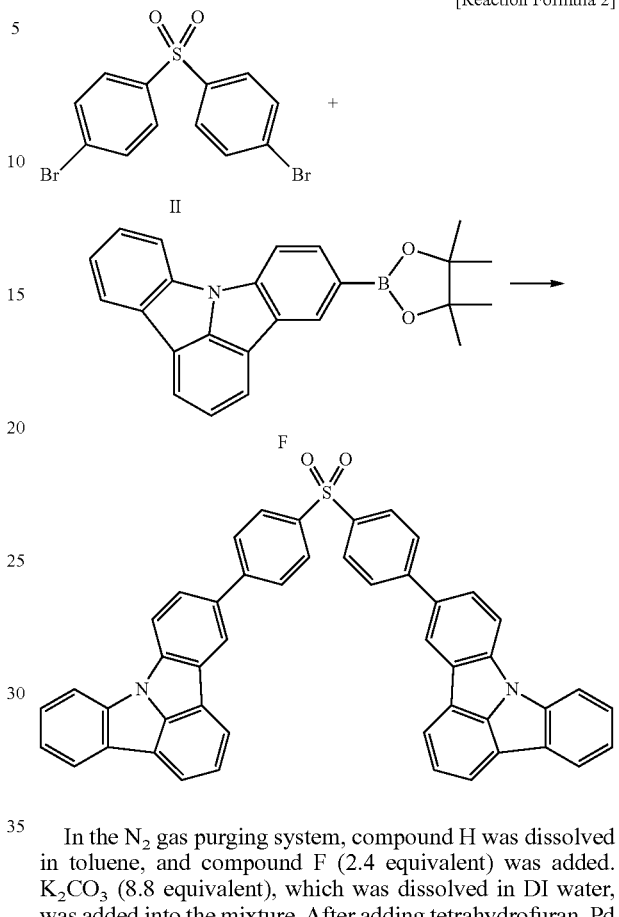

In the N₂ gas purging system, compound H was dissolved in toluene, and compound F (2.4 equivalent) was added. K₂CO₃ (8.8 equivalent), which was dissolved in DI water, was added into the mixture. After adding tetrahydrofuran, Pd (0.1 equivalent) was added. The mixture was refluxed and stirred under a temperature of 80° C. The mixture was extracted and was re-crystallized for separation of compound H, compound F, and the by-products. The resultant was columned by dichloromethane and hexane such that compound 2 was obtained.

3. Synthesis of Compound 3

(1) Compound H-1

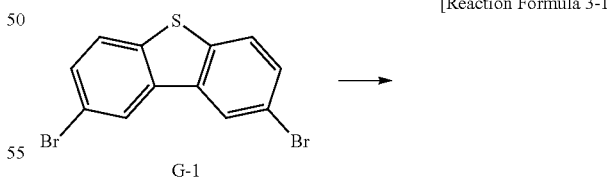

In the N₂ gas purging system, compound G-1 was put into acetic acid and was stirred. 30% hydrogen peroxide was excessively added. The mixture was refluxed for 8 hours under a temperature of 110° C., and the reaction was completed. The mixture was cooled in room temperature, and water was slowly added to be precipitate. The mixture was additionally stirred for about 30 minutes, and the precipitate was filtered. The resultant was washed by water such that compound H-1 was obtained.

(2) compound I-1

[Reaction Formula 3-2]

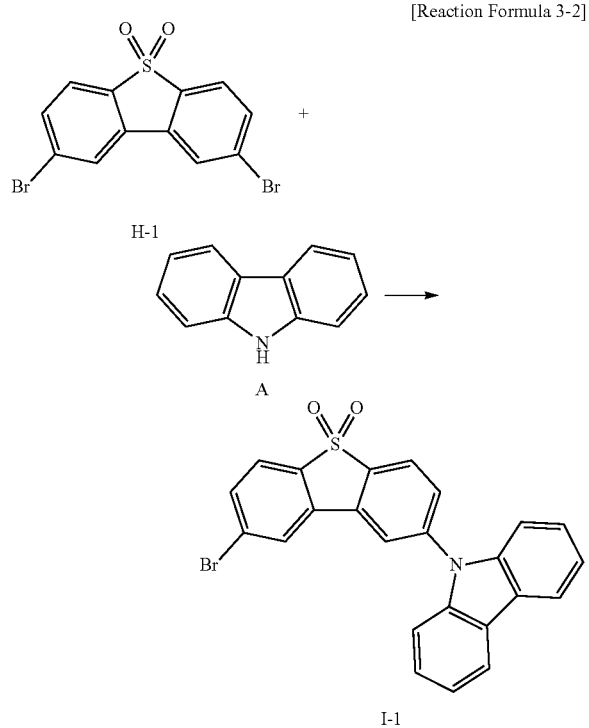

In the N₂ gas purging system, compound A (1 equivalent) was dissolved in 1,4-dioxane, and CuI and K₃PO₄ were added. Compound H-1 (1.1 equivalent) and trans-1,2-diaminocyclohexane were added into the flask including the compound A. The mixture was stirred and refluxed for 24 hours under a temperature of 110° C. After completion of the reaction, the mixture, which was cooled in room temperature, was extracted by using water and ethyl acetate. The resultant was columned by using the solvent of ethyl acetate and hexane such that compound I-1 was obtained.

(3) compound 3

[Reaction Formula 3-3]

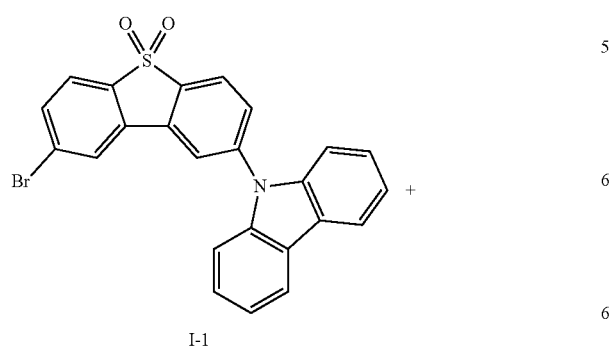

-continued

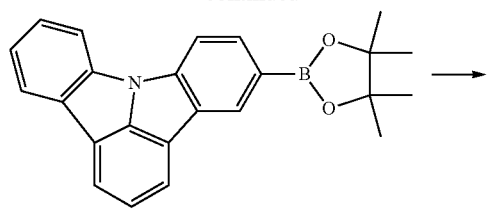

F

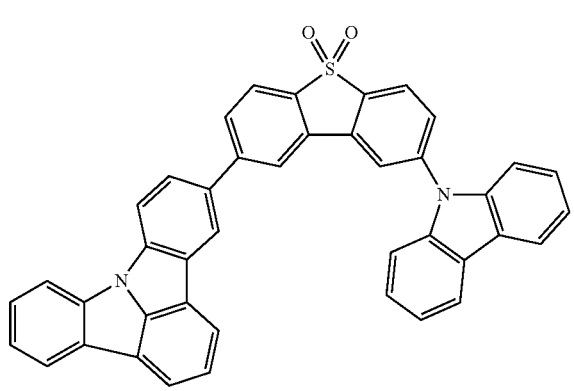

In the N₂ gas purging system, compound I-1 was dissolved in toluene, and compound F (1.2 equivalent) was added. K₂CO₃ (4.4 equivalent), which was dissolved in DI water, was added into the mixture. After adding tetrahydrofuran, Pd (0.05 equivalent) was added. The mixture was refluxed and stirred for 8 hours under a temperature of 80° C. The mixture was extracted and was re-crystallized for separation of compound I-1, compound F and the by-products. The resultant was columned by dichloromethane and hexane such that compound 3 was obtained.

4. synthesis of compound 4

[Reaction Formula 4]

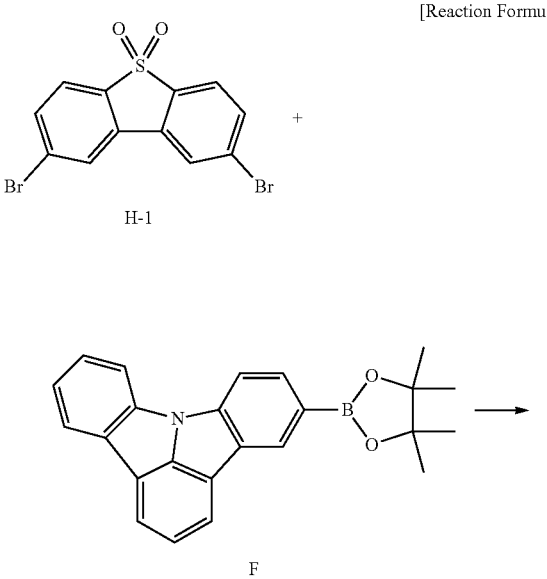

-continued

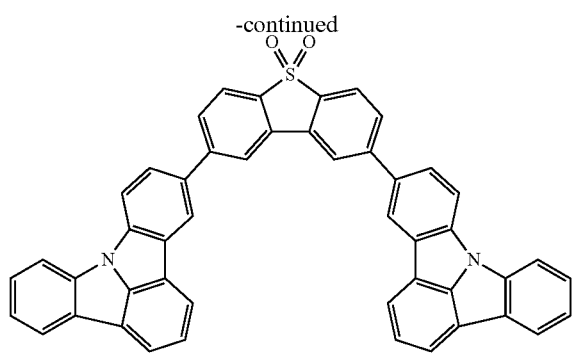

In the N₂ gas purging system, compound H-1 was dissolved in toluene, and compound F (2.4 equivalent) was added. K₂CO₃ (8.8 equivalent), which was dissolved in DI water, was added into the mixture. After adding tetrahydrofuran, Pd (0.1 equivalent) was added. The mixture was refluxed and stirred for 8 hours under a temperature of 80° C. The mixture was extracted and was re-crystallized for separation of compound H-1, compound F and the by-products. The resultant was columned by dichloromethane and hexane such that compound 4 was obtained.

5. synthesis of compound 5

(1) compound K

[Reaction Formula 5-1]

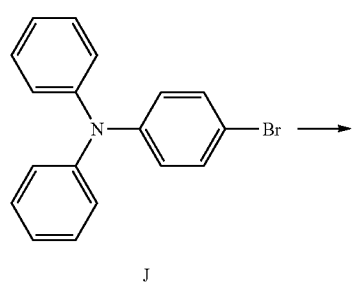

J

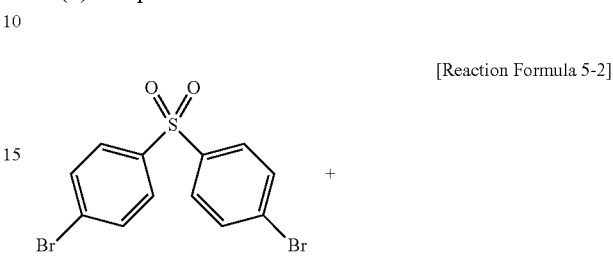

K

In the N₂ gas purging system, compound J was dissolved in tetrahydrofuran, and n-butyl-lithium (1.2 equivalent) was slowly added under a temperature of −78° C. The mixture was stirred for 1 hour under a temperature of −78° C. After additionally stirring the mixture for 2 hours under the room temperature, the mixture was cooled into a temperature of −78° C., and trimethyl-borate was added. The temperature of the mixture was slowly increased in room temperature and was stirred for 2 hours. Diluted hydrochloric acid (5.0%) was added into the mixture and stirred for 1 hour under a condition of pH 5 to 6. The solution was extracted by methylene chloride. The organic part was extracted by brine and DI water, and moisture was removed by MgSO₄. The organic solvent was removed such that compound K was obtained.

(2) compound L

[Reaction Formula 5-2]

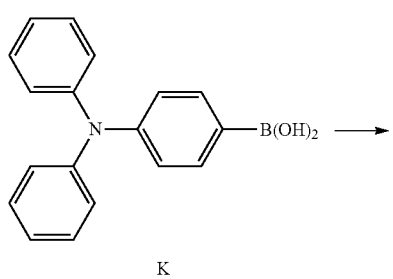

+

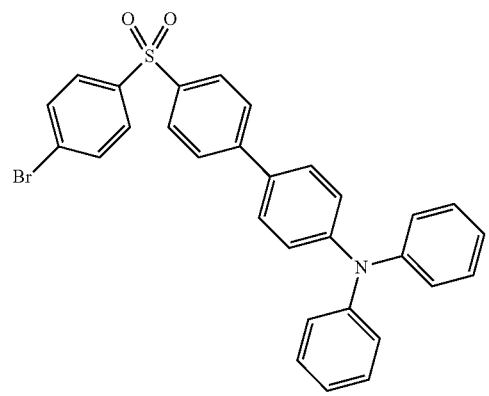

L

In the N₂ gas purging system, compound H was dissolved in toluene, and compound K (1.1 equivalent) was added. K₂CO₃ (4.4 equivalent), which was dissolved in DI water, was added into the mixture. After adding tetrahydrofuran, Pd (0.05 equivalent) was added. The mixture was refluxed and stirred under a temperature of 80° C. The mixture was extracted and was re-crystallized for separation of compound H, compound K, and the by-products. The resultant was columned by dichloromethane and hexane such that compound L was obtained.

(3) compound 5

[Reaction Formula 5-3]

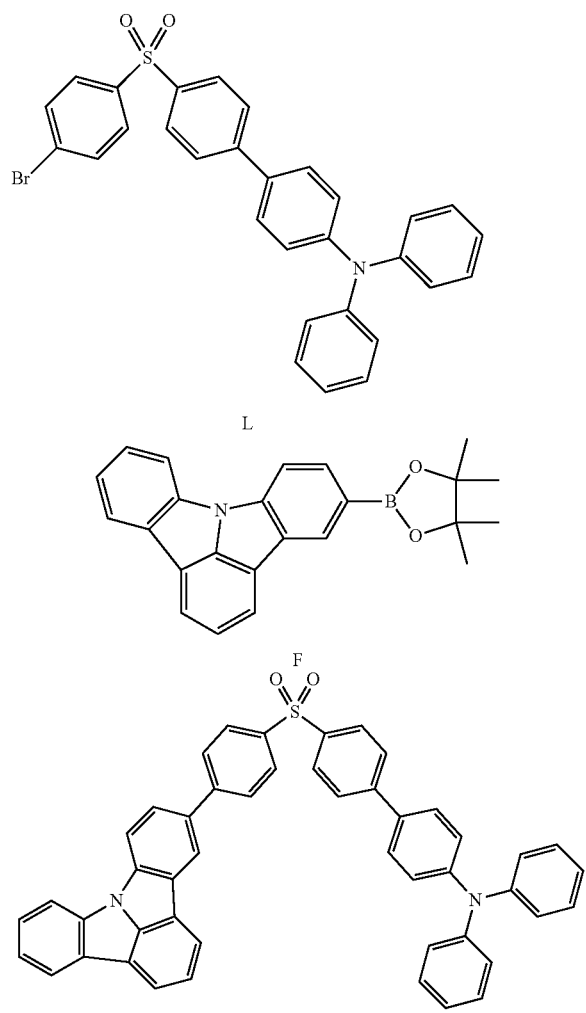

In the N₂ gas purging system, compound L was dissolved in toluene, and compound F (1.1 equivalent) was added. K₂CO₃ (4.4 equivalent), which was dissolved in DI water, was added into the mixture. After adding tetrahydrofuran, Pd (0.05 equivalent) was added. The mixture was refluxed and stirred under a temperature of 80° C. The mixture was extracted and was re-crystallized for separation of compound L, compound F and the by-products. The resultant was columned by dichloromethane and hexane such that compound 5 was obtained.

6. synthesis of compound 6
(1) compound L-1

[Reaction Formula 6-1]

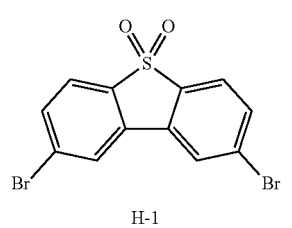

-continued

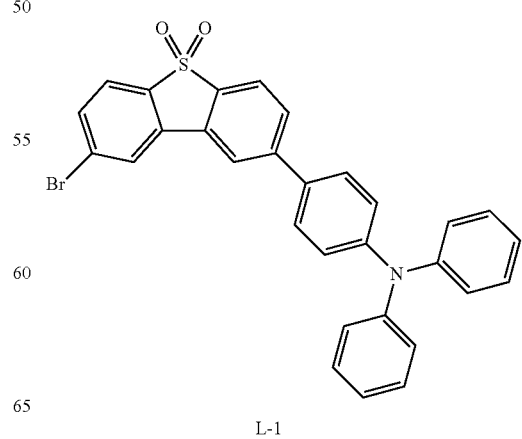

In the N₂ gas purging system, compound H-1 was dissolved in toluene, and compound K (1.1 equivalent) was added. K₂CO₃ (4.4 equivalent), which was dissolved in DI water, was added into the mixture. After adding tetrahydrofuran, Pd (0.05 equivalent) was added. The mixture was refluxed and stirred under a temperature of 80° C. The mixture was extracted and was re-crystallized for separation of compound H-1, compound K and the by-products. The resultant was columned by dichloromethane and hexane such that compound L-1 was obtained.

(2) compound 6

[Reaction Formula 6-2]

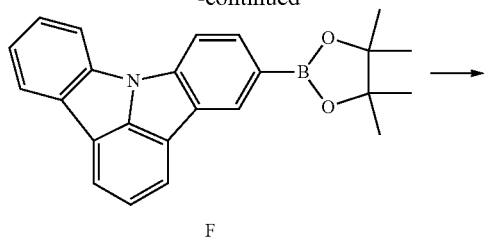

F

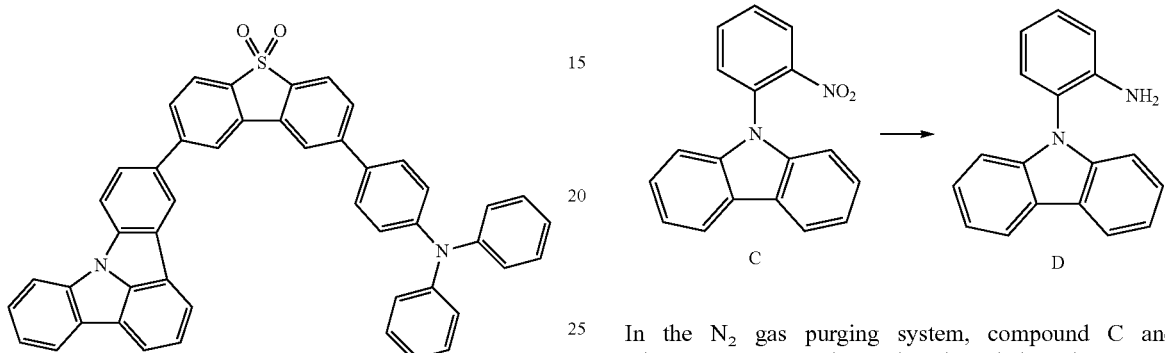

In the N₂ gas purging system, compound L-1 was dissolved in toluene, and compound F (1.1 equivalent) was added. K₂CO₃ (4.4 equivalent), which was dissolved in DI water, was added into the mixture. After adding tetrahydrofuran, Pd (0.05 equivalent) was added. The mixture was refluxed and stirred under a temperature of 80° C. The mixture was extracted and was re-crystallized for separation of compound L-1, compound F and the by-products. The resultant was columned by dichloromethane and hexane such that compound 6 was obtained.

7. synthesis of compound 7

(1) compound C

C. in the oil bath. 8 hours after, the mixture was put into iced DI water such that yellow solids were obtained. The yellow solids were filtered and extracted by using dichloromethane and DI water. Moisture was removed by MgSO₄, and the organic solvent was removed. The resultant was re-crystallized by using dichloromethane and methanol such that compound C was obtained.

(2) compound D

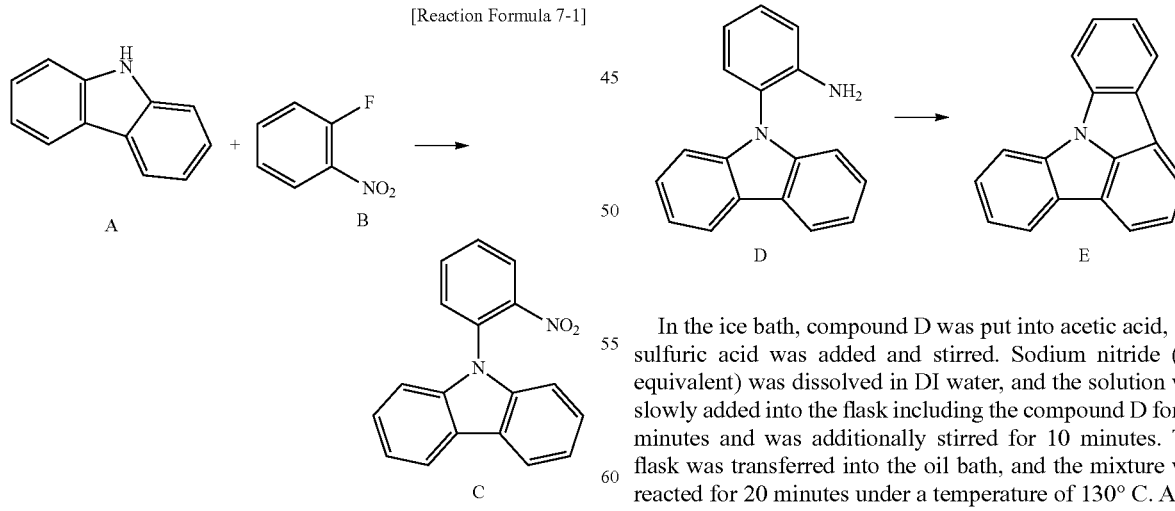

In the N₂ gas purging system, compound C and SnCl₂.2H₂O were put into ethanol, and the mixture was stirred for 8 hours under a temperature of 70° C. After completion of the reaction, the mixture was cooled into the room temperature. The mixture was added into 1N sodium hydroxide aqueous solution to obtain solids. The solids were filtered and dissolved in dichloromethane. 1N (equivalent per liter) sodium hydroxide aqueous solution was added to be extracted. The aqueous layer was removed to obtain an organic layer. The organic layer was extracted by DI water, and moisture was removed by MgSO₄. The organic solvent was removed such that compound D was obtained.

(3) compound E

In the N₂ gas purging system, compound A, compound B (1.1 equivalent) and cesium carbonate (1.5 equivalent) were put into dimethylsulfoxide, and the mixture was stirred. After stirring for about 2 hour in room temperature, the mixture was put into and stirred under a temperature of 60°

In the ice bath, compound D was put into acetic acid, and sulfuric acid was added and stirred. Sodium nitride (1.1 equivalent) was dissolved in DI water, and the solution was slowly added into the flask including the compound D for 15 minutes and was additionally stirred for 10 minutes. The flask was transferred into the oil bath, and the mixture was reacted for 20 minutes under a temperature of 130° C. After completion of the reaction, the mixture was cooled in room temperature, and DI water was put into the resultant to obtain the precipitates. The precipitates was filtered and washed by methanol. The filtered precipitated was columned and re-crystallized by using dichloromethane and methanol such that compound E was obtained.

(4) compound F

[Reaction Formula 7-4]

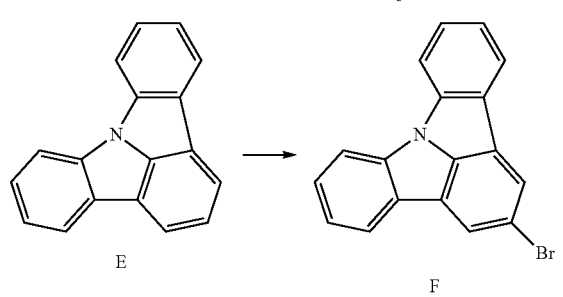

In the $N_2$ gas purging system, compound E and N-bromosuccinimide was put into dichloromethane in the flask, where the light was blocked out, and the mixture was stirred for 12 hours. After completion of the reaction, the mixture was extracted by using dichloromethane and DI water, and moisture was removed by $MgSO_4$. The resultant was refined such that compound F was obtained.

(5) compound G

[Reaction Formula 7-5]

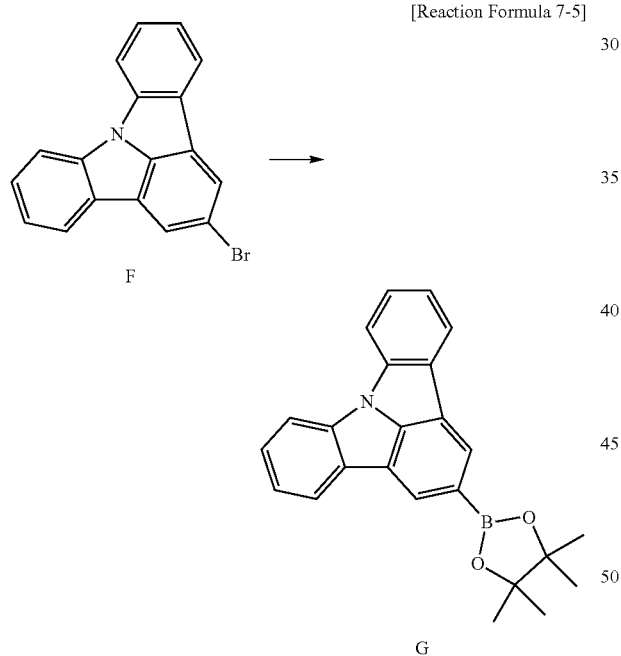

In the $N_2$ gas purging system, compound F, bis(pinacolate)diboron (1.2 equivalent), [1,1-bis(diphenylphosphineo)ferrocene]palladium(II), dichloride dichloromethane, 1,1-bis(diphenylphosphino)ferrocene and potassium acetate were put into the mixed solvent of 1,4-dioxane and toluene (1:1) in the flask, where the light was blocked out, and stirred. After the bubbles were disappeared, the mixture was stirred for 17 hours under a temperature of 120° C. in the oil bath. After completion of the reaction, the mixture was cooled in room temperature, and the solvent was removed. The resultant was washed by dichloromethane and refined such that compound G was obtained.

(6) compound I

[Reaction Formula 7-6]

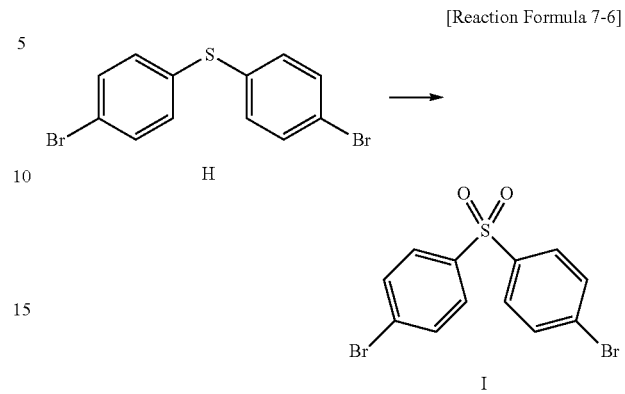

In the $N_2$ gas purging system, compound H was put into acetic acid and was stirred. 30% hydrogen peroxide was excessively added. The mixture was refluxed for 8 hours under a temperature of 110° C., and the reaction was completed. The mixture was cooled into the room temperature, and water was added to be precipitate. The mixture was stirred for about 30 minutes, and the precipitate was filtered. The resultant was washed by water such that compound I was obtained.

(7) compound J

[Reaction Formula 7-7]

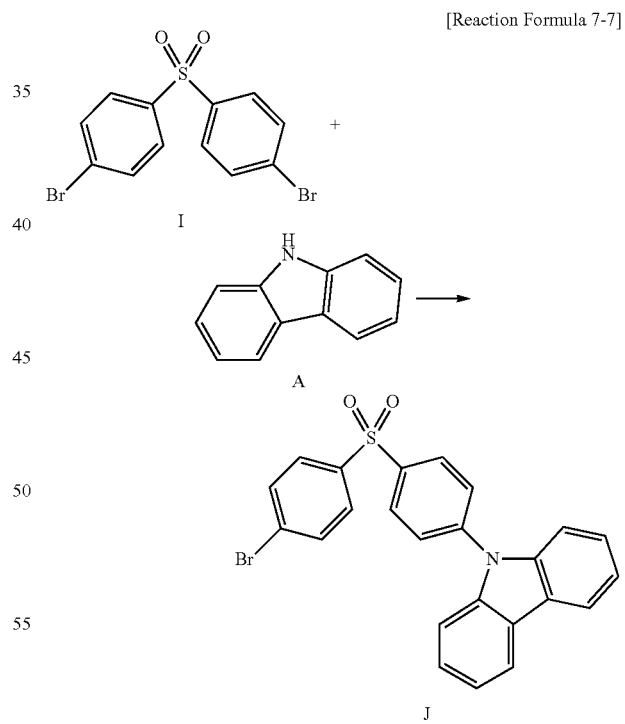

In the $N_2$ gas purging system, compound A (1 equivalent) was dissolved in 1,4-dioxane, and CuI and $K_3PO_4$ were added. Compound I (1.1 equivalent) and trans-1,2-diaminocyclohexane were added into the flask including the compound A. The mixture was stirred and refluxed for 24 hours under a temperature of 110° C. After completion of the reaction, the mixture, which was cooled in room temperature, was extracted by using water and ethyl acetate. The resultant was columned by using the solvent of ethyl acetate and hexane such that compound J was obtained.

(8) compound 7

[Reaction Formula 7-8]

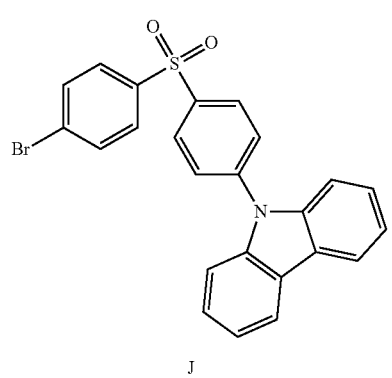

J

+

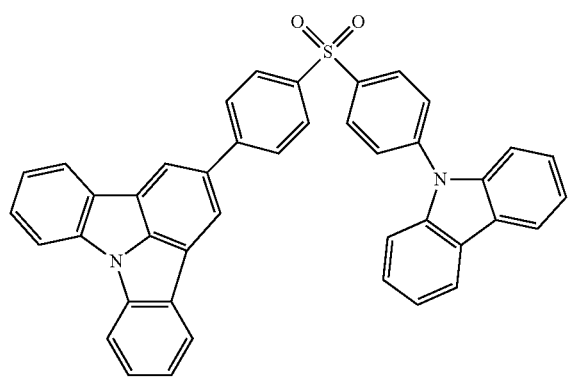

G

In the N₂ gas purging system, compound J was dissolved in toluene, and compound G (1.2 equivalent) was added. K₂CO₃ (4.4 equivalent), which was dissolved in DI water, was added into the mixture. After adding tetrahydrofuran, Pd (0.05 equivalent) was added. The mixture was refluxed and stirred under a temperature of 80° C. The mixture was extracted and was re-crystallized for separation of compound J, compound G and the by-products. The resultant was columned by dichloromethane and hexane such that compound 7 was obtained.

8. synthesis of compound 8

[Reaction Formula 8]

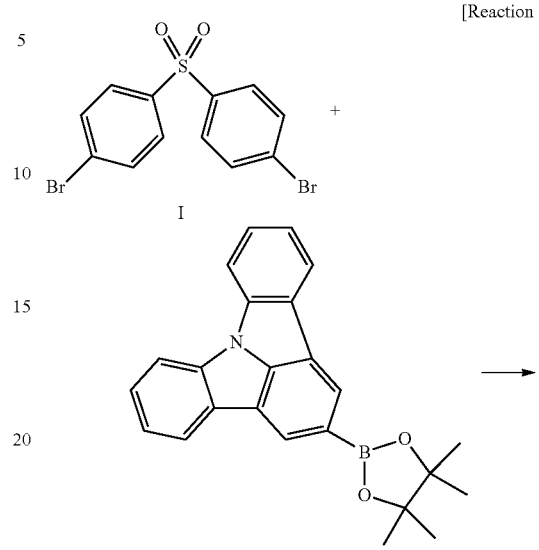

In the N₂ gas purging system, compound I was dissolved in toluene, and compound G (2.4 equivalent) was added. K₂CO₃ (8.8 equivalent), which was dissolved in DI water, was added into the mixture. After adding tetrahydrofuran, Pd (0.1 equivalent) was added. The mixture was refluxed and stirred under a temperature of 80° C. The mixture was extracted and was re-crystallized for separation of compound I, compound G and the by-products. The resultant was columned by dichloromethane and hexane such that compound 8 was obtained.

9. synthesis of compound 9

(1) compound I-1

[Reaction Formula 9-1]

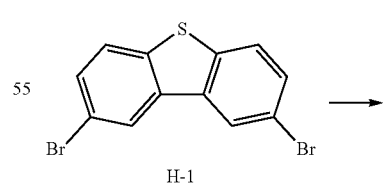

H-1

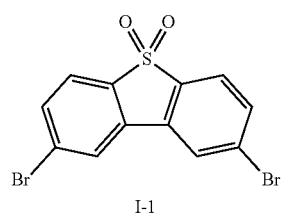

I-1

In the N₂ gas purging system, compound H-1 was put into acetic acid and was stirred. 30% hydrogen peroxide was excessively added. The mixture was refluxed for 8 hours under a temperature of 110° C., and the reaction was completed. The mixture was cooled in room temperature, and water was slowly added to be precipitate. The mixture was additionally stirred for about 30 minutes, and the precipitate was filtered. The resultant was washed by water such that compound I-1 was obtained.

(2) compound J-1

[Reaction Formula 9-2]

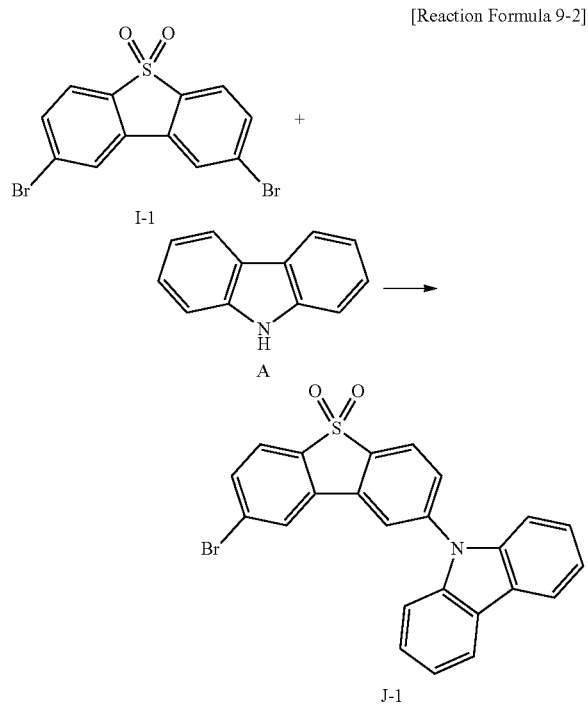

In the N₂ gas purging system, compound A (1 equivalent) was dissolved in 1,4-dioxane, and CuI and K₃PO₄ were added. Compound I-1 (1.1 equivalent) and trans-1,2-di-aminocyclohexane were added into the flask including the compound A. The mixture was stirred and refluxed for 24 hours under a temperature of 110° C. After completion of the reaction, the mixture, which was cooled in room temperature, was extracted by using water and ethyl acetate. The resultant was columned by using the solvent of ethyl acetate and hexane such that compound J-1 was obtained.

(3) compound 9

[Reaction Formula 9-3]

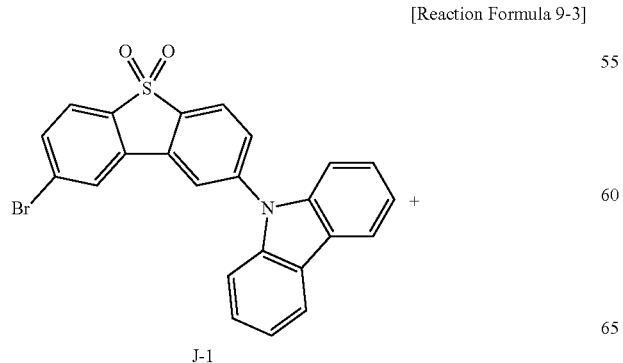

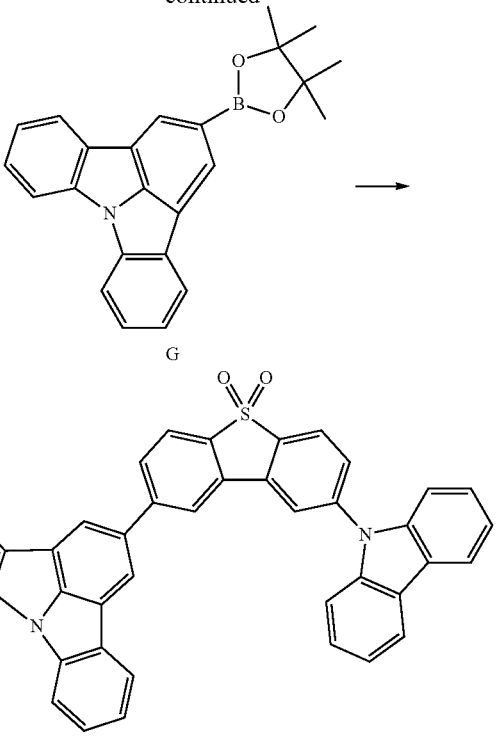

In the N₂ gas purging system, compound J-1 was dissolved in toluene, and compound G (1.2 equivalent) was added. K₂CO₃ (4.4 equivalent), which was dissolved in DI water, was added into the mixture. After adding tetrahydrofuran, Pd (0.05 equivalent) was added. The mixture was refluxed and stirred for 8 hours under a temperature of 80° C. The mixture was extracted and was re-crystallized for separation of compound J-1, compound G and the by-products. The resultant was columned by dichloromethane and hexane such that compound 9 was obtained.

10. synthesis of compound 10

[Reaction Formula 10]

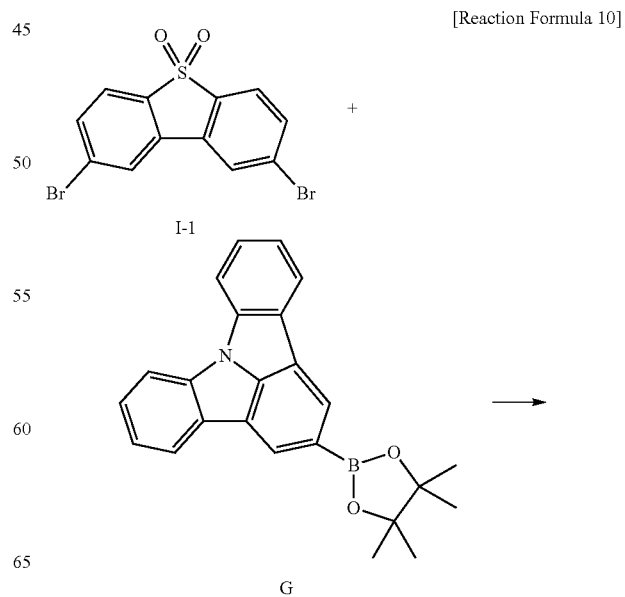

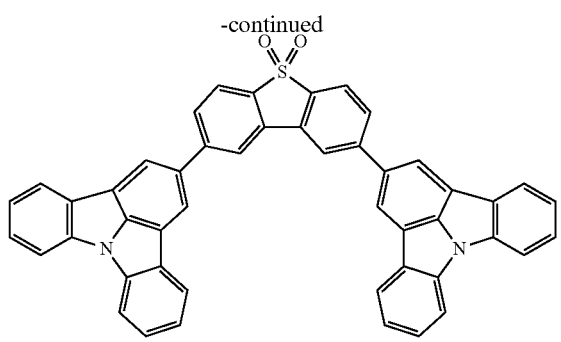

In the N₂ gas purging system, compound I-1 was dissolved in toluene, and compound G (2.4 equivalent) was added. K₂CO₃ (8.8 equivalent), which was dissolved in DI water, was added into the mixture. After adding tetrahydrofuran, Pd (0.1 equivalent) was added. The mixture was refluxed and stirred for 8 hours under a temperature of 80° C. The mixture was extracted and was re-crystallized for separation of compound I-1, compound G and the by-products. The resultant was columned by dichloromethane and hexane such that compound 10 was obtained.

11. synthesis of compound 11

(1) compound L

[Reaction Formula 11-1]

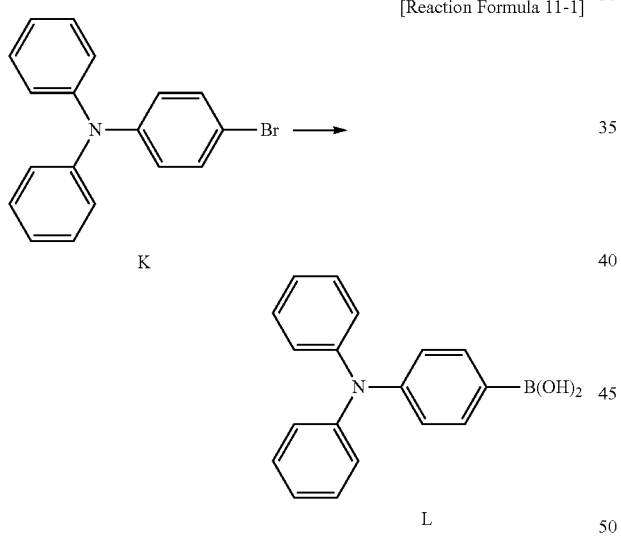

In the N₂ gas purging system, compound K was dissolved in tetrahydrofuran, and n-butyl-lithium (1.2 equivalent) was slowly added under a temperature of −78° C. The mixture was stirred for 1 hour under a temperature of −78° C. After additionally stirring the mixture for 2 hours under the room temperature, the mixture was cooled into a temperature of −78° C., and trimethyl-borate was added. The temperature of the mixture was slowly increased in room temperature and was stirred for 2 hours. Diluted hydrochloric acid (5.0%) was added into the mixture and stirred for 1 hour under a condition of pH 5 to 6. The solution was extracted by methylene chloride. The organic part was extracted by brine and DI water, and moisture was removed by MgSO₄. The organic solvent was removed such that compound L was obtained.

(2) compound M

[Reaction Formula 11-2]

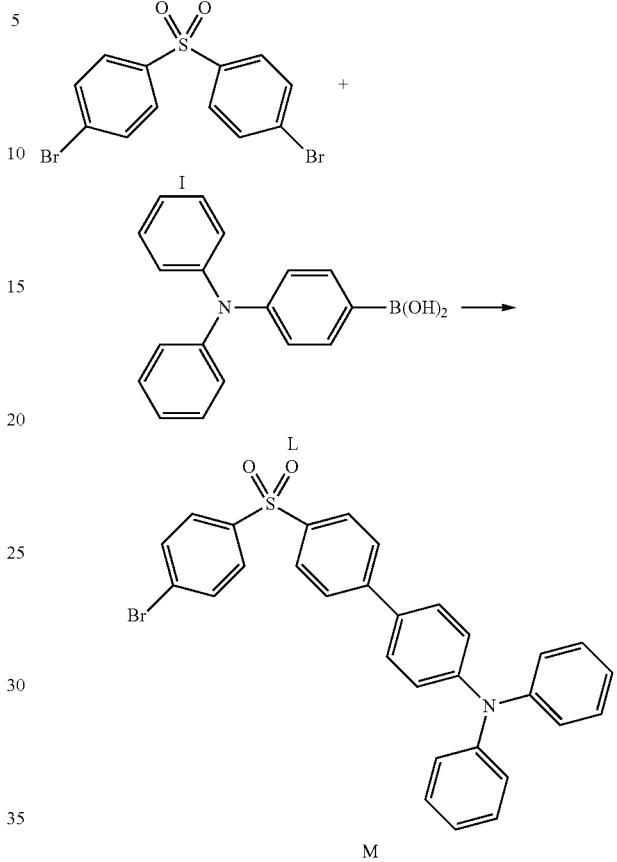

In the N₂ gas purging system, compound I was dissolved in toluene, and compound L (1.1 equivalent) was added. K₂CO₃ (4.4 equivalent), which was dissolved in DI water, was added into the mixture. After adding tetrahydrofuran, Pd (0.05 equivalent) was added. The mixture was refluxed and stirred under a temperature of 80° C. The mixture was extracted and was re-crystallized for separation of compound I, compound L and the by-products. The resultant was columned by dichloromethane and hexane such that compound M was obtained.

(3) compound 11

[Reaction Formula 11-3]

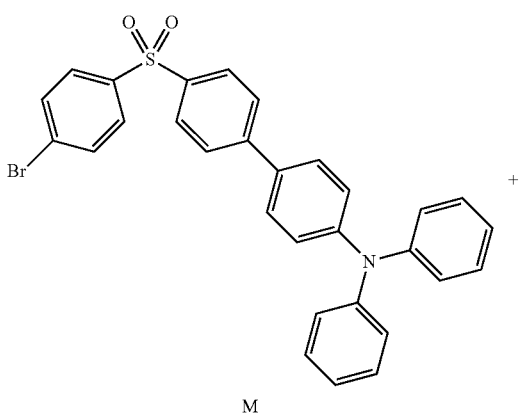

-continued

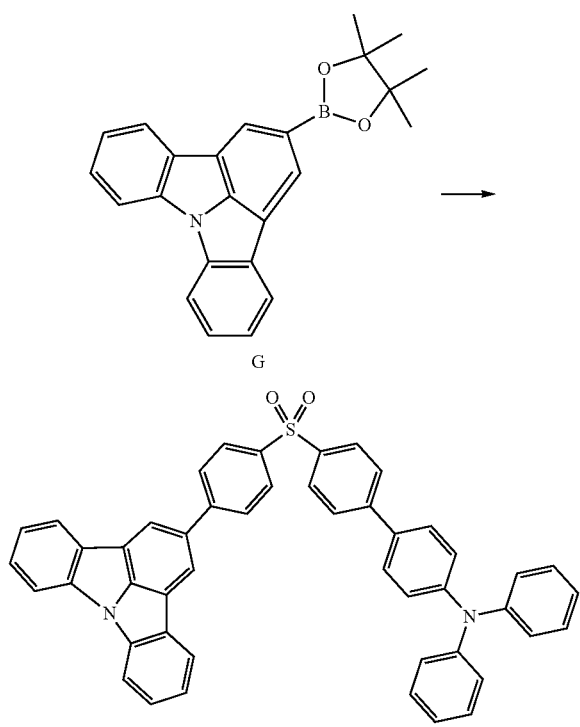

G

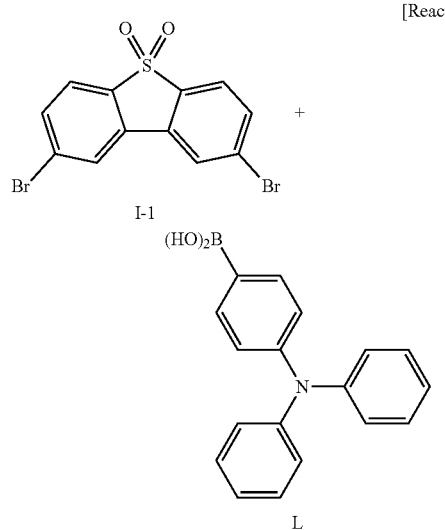

In the N₂ gas purging system, compound M was dissolved in toluene, and compound G (1.1 equivalent) was added. K₂CO₃ (4.4 equivalent), which was dissolved in DI water, was added into the mixture. After adding tetrahydrofuran, Pd (0.05 equivalent) was added. The mixture was refluxed and stirred under a temperature of 80° C. The mixture was extracted and was re-crystallized for separation of compound M, compound G and the by-products. The resultant was columned by dichloromethane and hexane such that compound 11 was obtained.

12. synthesis of compound 12

(1) compound M-1

[Reaction Formula 12-1]

-continued

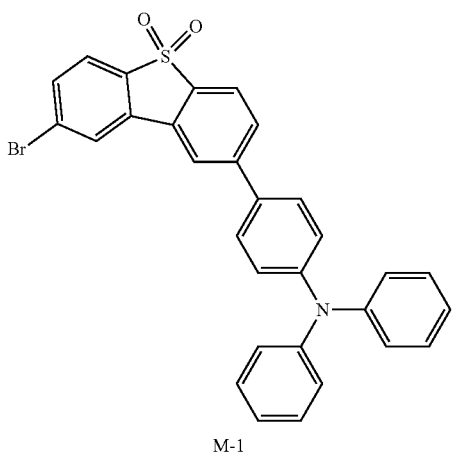

M-1

In the N₂ gas purging system, compound I-1 was dissolved in toluene, and compound L (1.1 equivalent) was added. K₂CO₃ (4.4 equivalent), which was dissolved in DI water, was added into the mixture. After adding tetrahydrofuran, Pd (0.05 equivalent) was added. The mixture was refluxed and stirred under a temperature of 80° C. The mixture was extracted and was re-crystallized for separation of compound I-1, compound L and the by-products. The resultant was columned by dichloromethane and hexane such that compound M-1 was obtained.

(2) compound 12

[Reaction Formula 12-2]

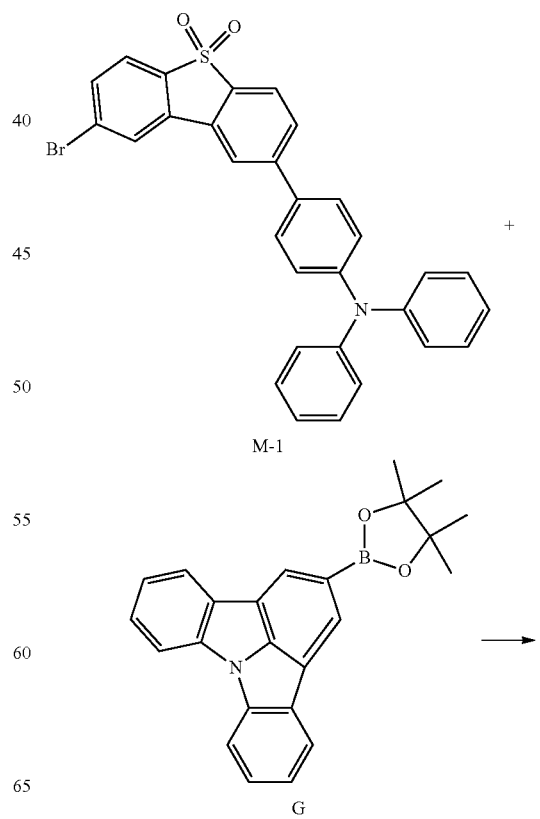

-continued

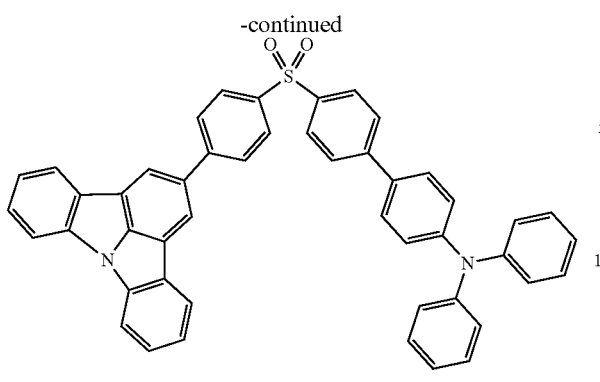

In the N₂ gas purging system, compound M-1 was dissolved in toluene, and compound G (1.1 equivalent) was added. K₂CO₃ (4.4 equivalent), which was dissolved in DI water, was added into the mixture. After adding tetrahydrofuran, Pd (0.05 equivalent) was added. The mixture was refluxed and stirred under a temperature of 80° C. The mixture was extracted and was re-crystallized for separation of compound M-1, compound G and the by-products. The resultant was columned by dichloromethane and hexane such that compound 12 was obtained.

The mass spectrum data of the above compounds 1 to 12 are listed in Table 2.

TABLE 2

|       |                  | Calculation | Found (M(H+)) |
|-------|------------------|-------------|---------------|
| Com1  | $C_{42}H_{26}N_2O_2S$ | 622.17 | 623.05 |
| Com2  | $C_{48}H_{28}N_2O_2S$ | 696.19 | 697.47 |
| Com3  | $C_{42}H_{24}N_2O_2S$ | 620.16 | 620.98 |
| Com4  | $C_{48}H_{26}N_2O_2S$ | 694.17 | 695.28 |
| Com5  | $C_{48}H_{32}N_2O_2S$ | 700.22 | 701.39 |
| Com6  | $C_{48}H_{30}N_2O_2S$ | 698.20 | 699.05 |
| Com7  | $C_{42}H_{26}N_2O_2S$ | 622.17 | 622.93 |
| Com8  | $C_{48}H_{28}N_2O_2S$ | 696.19 | 697.31 |
| Com9  | $C_{42}H_{24}N_2O_2S$ | 620.16 | 621.20 |
| Com10 | $C_{48}H_{26}N_2O_2S$ | 694.17 | 695.08 |
| Com11 | $C_{48}H_{32}N_2O_2S$ | 700.22 | 701.16 |
| Com12 | $C_{48}H_{30}N_2O_2S$ | 698.20 | 699.49 |

The emission properties of the above compounds 1, 2, 9, and 10 (Com1, Com2, Com9, and Com10) are measured and the results are listed in Table 3 and shown in FIGS. 2A to 2D. (Quantarus tau apparatus of Hamamatsu Co., Ltd. O₂ free condition.)

TABLE 3

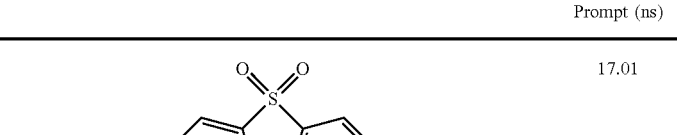

|  | Prompt (ns) | Delayed (ns) |
|---|---|---|
| Com1 | 17.01 | 4706.58 |
| Com2 | 10.44 | 311.20 |

TABLE 3-continued

| | Prompt (ns) | Delayed (ns) |
|---|---|---|
| 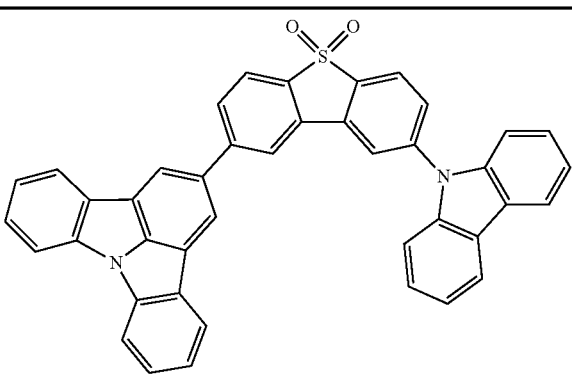 Com9 | 62.05 | 7273.16 |
| 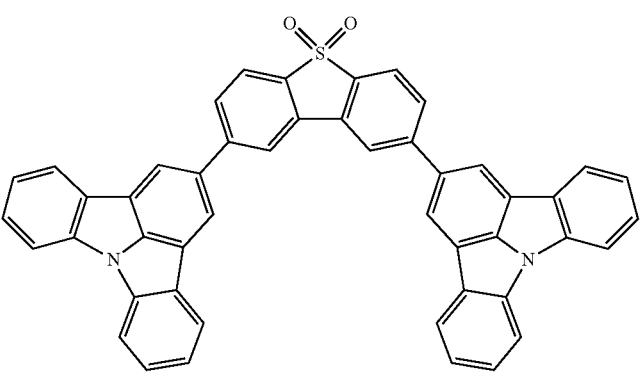 Com10 | 12.65 | 2658.03 |

As shown in Table 3 and FIGS. 2A to 2D, the delayed fluorescence compounds (Com1, Com2, Com9, and Com10) of the present invention show the delayed fluorescent emission of hundreds to thousands of nano-seconds (ns).

As mentioned above, the delayed fluorescence compound of the present invention is activated by the field such that the excitons in the singlet state "$S_1$" and the triplet state "$T_1$" are transited into the intermediated state "$I_1$". As a result, both the exciton in the singlet state "$S_1$" and the exciton in the triplet state "$T_1$" are engaged in the emission.

The FADF compound is a single molecule compound having the electron donor moiety and the electron acceptor moiety in the single molecule such that the charge transfer is easily generated. In the FADF compound with particular conditions, the charge can be separated from the electron donor moiety to the electron acceptor moiety.

The FADF compound is activated by outer factors. It can be verified by comparing the absorption peak and the emission peak of the solution of the compounds.

$$\Delta v = v_{abs} - v_{fl} = \frac{2\Delta\mu^2}{hca^3}\Delta f + \text{constant} \quad \text{(Lippert–Mataga equation)}$$

In the above equation, "$\Delta v$" is the Stock-shift value, and "$v_{abs}$" and "$v_{fl}$" are the wave-number of the maximum absorption peak and the maximum emission peak, respectively. "h" is Planck's constant, "c" is the velocity of light, "a" is the onsager cavity radius, and "$\Delta\mu$" is a difference between the dipole moment of the excited state and the dipole moment of the ground state. ($\Delta\mu=\mu_e-\mu_g$)

"$\Delta f$" is a value indicating the orientational polarizability of the solvent and may be a function of the dielectric constant of the solvent ($\in$) and the refractive index of the solvent (n).

$$\Delta f = \frac{\varepsilon - 1}{2\varepsilon + 1} - \frac{n^2 - 1}{2n^2 + 1}$$

Since the intensity of dipole moment in the excited state is determined by the peripheral polarity (e.g., the polarity of the solvent), the FADF can be verified by comparing the absorption peak and the emission peak of the solution of the compounds.

The orientational polarizability ($\Delta f$) of the mixed solvent can be calculated by using the orientational polarizability of each pure solvent and their mole fraction. When "$\Delta f$" and "$\Delta v$" are linearly plotted by using above "Lippert-Mataga equation", the compound may provide the FADF emission.

Namely, when the FADF complex is stabilized according to the orientational polarizability of the solvent, the emission peak is shifted in a long wavelength according to the degree of the stabilization. Accordingly, when the compound provides the FADF emission, "$\Delta f$" and "$\Delta v$" are plotted in a linear line. When "$\Delta f$" and "$\Delta v$" are plotted in a linear line, the compound provides the FADF emission.

In the delayed fluorescence compound of the present invention, the 25% excitons in the singlet state and the 75% excitons in the triplet state are transited into the intermediate state by an outer force, i.e., a field generated when the OLED is driven. (Intersystem crossing.) The excitons in the intermediate state are transited into the ground state such that the emitting efficiency is improved. Namely, in the fluorescent compound, since the singlet exciton and the triplet exciton are engaged in the emission, the emitting efficiency is improved.

OLED

An ITO layer is deposited on a substrate and washed to form an anode (3 mm*3 mm) The substrate is loaded in a vacuum chamber, and a hole injecting layer (40 Å, NPB(N, N'-di(naphthalen-1-yl)-N,N'-diphenyl-benzidine)), a hole transporting layer (10 Å, mCP(N,N'-Dicarbazolyl-3,5-benzene)), an emitting material layer (200 Å, host (bis{2-[di(phenyl)phosphino]phenyl}ether oxide) and dopant (12%)), an electron transporting layer (300 Å, 1,3,5-tri(phenyl-2-benzimidazole)-benzene), an electron injecting layer (10 Å, LiF), and a cathode (Al) are sequentially formed on the anode under a base pressure of about $10^{-6}$ to $10^{-7}$ Torr.

(1) Comparative Example (Ref)

The reference compound in Formula 6 is used as the dopant to form the OLED.

(2) Example 1 (Ex1)

The compound 1 is used as the dopant to form the OLED.

(3) Example 2 (Ex2)

The compound 2 is used as the dopant to form the OLED.

(4) Example 3 (Ex3)

The compound 3 is used as the dopant to form the OLED.

(5) Example 4 (Ex4)

The compound 6 is used as the dopant to form the OLED.

(6) Example 5 (Ex5)

The compound 7 is used as the dopant to form the OLED.

(7) Example 6 (Ex6)

The compound 9 is used as the dopant to form the OLED.

(8) Example 7 (Ex7)

The compound 10 is used as the dopant to form the OLED.

(9) Example 8 (Ex8)

The compound 11 is used as the dopant to form the OLED.

[Formula 6]

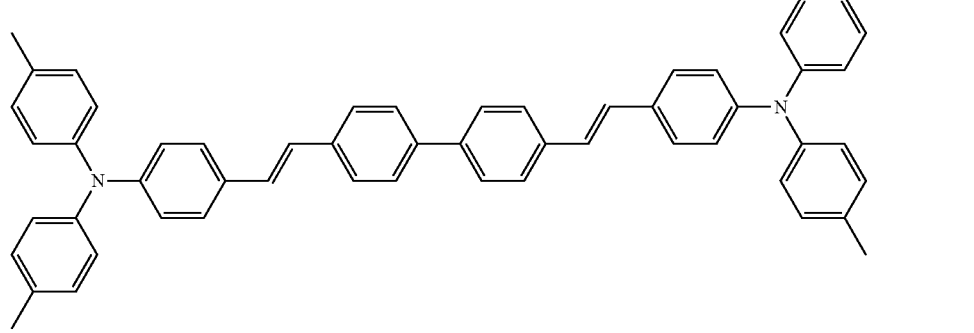

TABLE 4

|  | Voltage (V) | Cd/A | lm/W | EQE (%) | CIE (X) | CIE (Y) |
| --- | --- | --- | --- | --- | --- | --- |
| Ref | 7.94 | 4.84 | 1.91 | 2.99 | 0.182 | 0.169 |
| Ex1 | 6.14 | 12.85 | 6.57 | 7.27 | 0.165 | 0.116 |
| Ex2 | 5.92 | 12.45 | 6.60 | 6.92 | 0.168 | 0.111 |
| Ex3 | 5.66 | 10.19 | 5.66 | 6.43 | 0.173 | 0.122 |
| Ex4 | 5.95 | 10.72 | 5.66 | 5.18 | 0.167 | 0.121 |
| Ex5 | 5.62 | 10.22 | 5.71 | 6.42 | 0.156 | 0.138 |
| Ex6 | 5.25 | 11.76 | 7.03 | 6.99 | 0.169 | 0.104 |
| Ex7 | 5.86 | 12.54 | 6.71 | 6.95 | 0.164 | 0.113 |
| Ex8 | 5.68 | 10.00 | 5.53 | 6.33 | 0.178 | 0.161 |

As shown in Table 4, in the OLEDs using the compounds of the present invention (Ex1 to Ex8), the color purity and the emitting efficiency are improved.

FIG. 3 is a schematic cross-sectional view of an OLED according to the invention.

As shown in FIG. 3, the OLED "E" is formed on a substrate (not shown). The OLED "E" includes a first electrode 110 as an anode, a second electrode 130 as a cathode and an organic emitting layer 120 therebetween.

Although not shown, an encapsulation film, which includes at least one inorganic layer and at least one organic layer and covers the OLED "E", and a cover window on the encapsulation film may be further formed to form a display device including the OLED "E". The substrate, the encapsulation film and the cover window may have a flexible property such that a flexible display device may be provided.

The first electrode 110 is formed of a material having a relatively high work function, and the second electrode 130 is formed of a material having a relatively low work function. For example, the first electrode 110 may be formed of indium-tin-oxide (ITO), and the second electrode 130 may be formed of aluminum (Al) or Al alloy (AlNd). The organic emitting layer 120 may include red, green, and blue emitting patterns.

The organic emitting layer 120 may have a single-layered structure. Alternatively, to improve the emitting efficiency, the organic emitting layer 120 includes a hole injection layer (HIL) 121, a hole transporting layer (HTL) 122, an emitting material layer (EML) 123, an electron transporting layer (ETL) 124, and an electron injection layer (EIL) 125 sequentially stacked on the first electrode 110.

At least one selected from the HIL 121, the HTL 122, the EML 123, the ETL 124, and the EIL 125 includes the delayed fluorescence compound in the Formula 1.

For example, the EML 123 may include the delayed fluorescence compound in the Formula 1. The delayed fluorescence compound acts as the dopant, and the EML 123 may further include a host to emit the blue light. In this instance, the dopant has about 1 to 30 weight % with respect to the host.

A difference between the HOMO of the host "$HOMO_{Host}$" and the HOMO of the dopant "$HOMO_{Dopant}$" or a difference between the LUMO of the host "$LUMO_{Host}$" and the LUMO of the dopant "$LUMO_{Dopant}$" is less than 0.5 eV. ($HOMO_{Host}-HOMO_{Dopant}|\leq 0.5$ eV or $|LUMO_{Host}-LUMO_{Dopant}|\leq 0.5$ eV.) In this instance, the charge transfer efficiency from the host to the dopant may be improved.

For example, the host, which meets the above condition, may be selected from materials in Formula 7. (Bis[2-(diphenylphosphino)phenyl]ether oxide (DPEPO), 2,8-bis(diphenylphosphoryl)dibenzothiophene (PPT), 2,8-di(9H-carbazol-9-yl)dibenzothiophene (DCzDBT), m-bis(carbazol-9-yl)biphenyl (m-CBP), Diphenyl-4-triphenylsilylphenyl-phosphine oxide (TPSO1), 9-(9-phenyl-9H-carbazol-6-yl)-9H-carbazole (CCP) in order.)

[Formula 7]

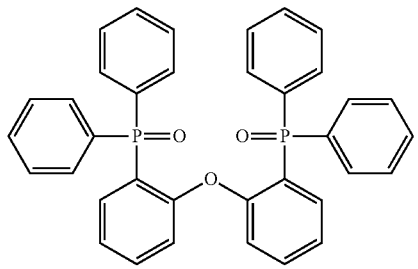

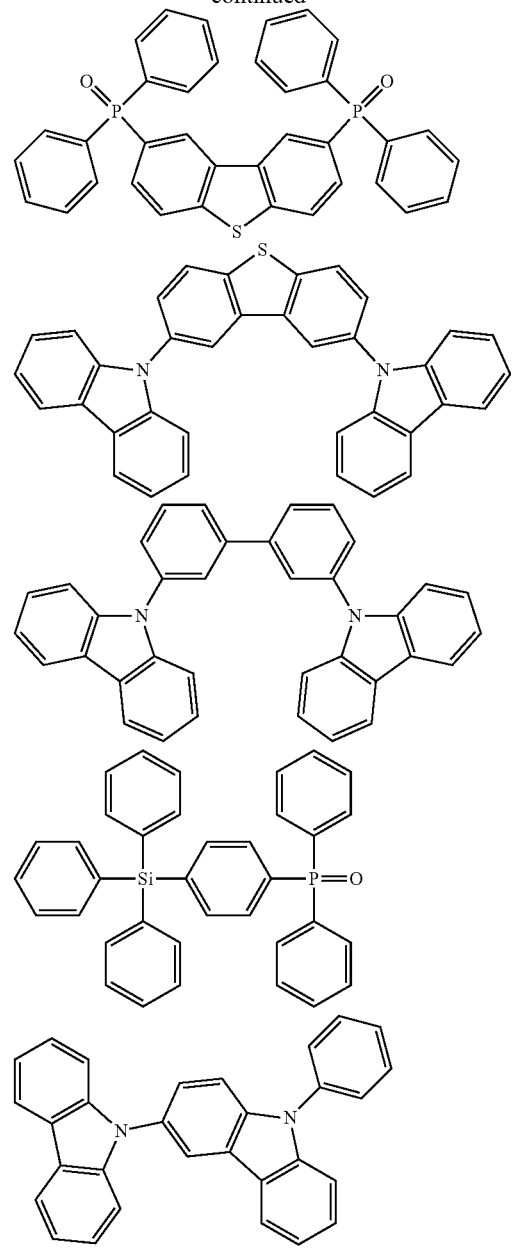

The triplet energy of the dopant is smaller than the triplet energy of the host, and a difference between the singlet energy of the dopant and the triplet energy of the dopant is less than 0.3 eV. ($\Delta E_{ST}\leq 0.3$ eV.) As the difference "$\Delta E_{ST}$" is smaller, the emitting efficiency is higher. In the delayed fluorescence compound of the present invention, even if the difference "$\Delta E_{ST}$" between the singlet energy of the dopant and the triplet energy of the dopant is about 0.3 eV, which is relatively large, the excitons in the singlet state "S1" and the excitons in the triplet state "T1" can be transited into the intermediate state "I1".

On the other hand, the delayed fluorescence compound of the present invention may act as a host in the EML 124 and the EML 123 may further include a dopant to emit the blue light. In this instance, the dopant has about 1 to 30 weight % with respect to the host. Since the development of the blue host having excellent properties is insufficient, the delayed fluorescence compound of the present invention may be used as the host to increase the degree of freedom for the host. In this instance, the triplet energy of the dopant may be smaller than the triplet energy of the host of the delayed fluorescence compound of the present invention.

The EML 123 may include a first dopant of the delayed fluorescence compound of the present invention, a host, and a second dopant. The weight % summation of the first and second dopants may be about 1 to 30 to emit the blue light. In this instance, the emitting efficiency and the color purity may be further improved.

In this instance, the triplet energy of the first dopant, i.e., the delayed fluorescence compound of the present invention, may be smaller than the triplet energy of the host, and larger than the triplet energy of the second dopant. In addition, a difference between the singlet energy of the first dopant and the triplet energy of the first dopant is less than 0.3 eV. ($\Delta E_{ST} \leq 0.3$ eV.) As the difference "$\Delta E_{ST}$" is smaller, the emitting efficiency is higher. In the delayed fluorescence compound of the present invention, even if the difference "$\Delta E_{ST}$" between the singlet energy of the dopant and the triplet energy of the dopant is about 0.3 eV, which is relatively large, the excitons in the singlet state "$S_1$" and the excitons in the triplet state "$T_1$" can be transited into the intermediate state "$I_1$".

As mentioned above, since the delayed fluorescence compound of the present invention includes the first and second electron donor moieties and the electron acceptor, the charge transfer in the molecule is easily generated such that the emitting efficiency of the compound is improved. In addition, the dipole from the first and second electron donor moieties to the electron acceptor moiety is generated such that the dipole moment in the molecule is increased. As a result, the emitting efficiency is further improved. Moreover, in the delayed fluorescent compound of the present invention, the excitons in the triplet state are engaged in the emission such that the emitting efficiency of the delayed fluorescent compound is increased.

Accordingly, the OLED and the display device using or including the delayed fluorescence compound of the present invention has an advantage in the emitting efficiency.

It will be apparent to those skilled in the art that various modifications and variations can be made in the embodiment of the invention without departing from the spirit or scope of the invention. Thus, it is intended that the embodiment of the invention cover the modifications and variations of this invention provided they come within the scope of the appended claims and their equivalents.

What is claimed is:

1. A delayed fluorescence compound, consisting of:
a first electron donor moiety of indolo-[3,2,1-j,k]carbazole;
a second electron donor moiety selected from the group consisting of indolo-[3,2,1-j,k]carbazole, carbazole, and triphenylamine; and
an electron acceptor moiety selected from the group consisting of dibenzothiophene sulfone and diphenyl sulfone,
wherein the first electron donor moiety and the second electron donor moiety are directly attached to the electron acceptor moiety, and the electron acceptor moiety is attached to a third position or a sixth position of the first electron donor moiety.

2. A delayed fluorescence compound of Formula 1:

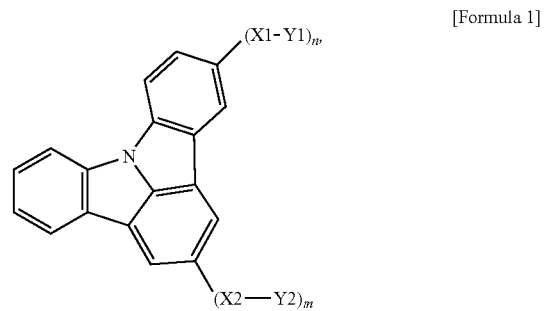

[Formula 1]

wherein one of m and n is 1, and the other of m and n is 0, and wherein each of X1 and X2 is independently selected from Formula 2, and each of Y1 and Y2 is independently selected from Formula 3:

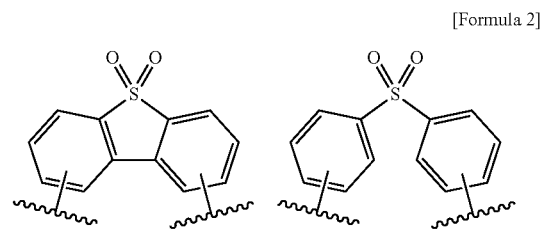

[Formula 2]

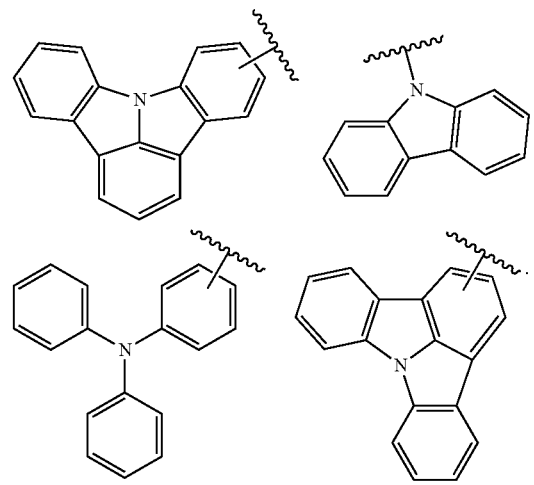

[Formula 3]

3. The delayed fluorescence compound according to claim 2, wherein a difference between a singlet energy of the delayed fluorescence compound and a triplet energy of the delayed fluorescence compound is less than 0.3 eV.

4. An organic light emitting diode, comprising:
a first electrode;
a second electrode facing the first electrode; and
an organic emitting layer between the first electrode and the second electrode, the organic emitting layer including a delayed fluorescence compound,
wherein the delayed fluorescence compound consists of a first electron donor moiety of indolo-[3,2,1-j,k]carbazole, a second electron donor moiety selected from the group consisting of indolo-[3,2,1-j,k]carbazole, carbazole, and triphenylamine, and an electron acceptor moiety selected from the group consisting of dibenzothiophene sulfone and diphenyl sulfone, wherein the first electron donor moiety and the second electron donor moiety are directly attached to the electron acceptor moiety, and the electron acceptor moiety is attached to a third position or a sixth position of the first electron donor moiety.

5. The organic light emitting diode according to claim 4, wherein the organic emitting layer includes a hole injection layer (HIL), a hole transporting layer (HTL), an emitting material layer (EML), an electron transporting layer (ETL), and an electron injection layer (EIL), and wherein at least one from the HIL, the HTL, the EML, the ETL, and the EIL includes the delayed fluorescence compound.

6. The organic light emitting diode according to claim 4, wherein a difference between a singlet energy of the delayed fluorescence compound and a triplet energy of the delayed fluorescence compound is less than 0.3 eV.

7. The organic light emitting diode according to claim 4, wherein the organic emitting layer further includes a host, and the delayed fluorescence compound is used as a dopant.

8. The organic light emitting diode according to claim 7, wherein a difference between a highest occupied molecular orbital (HOMO) of the host and a HOMO of the dopant or a difference between a lowest unoccupied molecular orbital (LUMO) of the host and a LUMO of the dopant is less than 0.5 eV.

9. The organic light emitting diode according to claim 4, wherein the organic emitting layer further includes a dopant, and the delayed fluorescence compound is used as a host.

10. The organic light emitting diode according to claim 4, wherein the organic emitting layer further includes a host and a first dopant, and the delayed fluorescence compound is used as a second dopant, and wherein a triplet energy of the second dopant is smaller than a triplet energy of the host and larger than a triplet energy of the first dopant.

11. An organic light emitting diode, comprising:

a first electrode;

a second electrode facing the first electrode; and an organic emitting layer between the first electrode and the second electrode, the organic emitting layer including a delayed fluorescence compound of Formula 1:

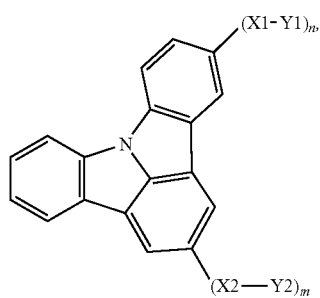

[Formula 1]

wherein one of m and n is 1, and the other of m and n is 0, and wherein each of X1 and X2 is independently selected from Formula 2, and each of Y1 and Y2 is independently selected from Formula 3:

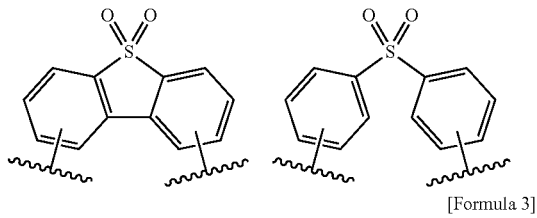

[Formula 2]

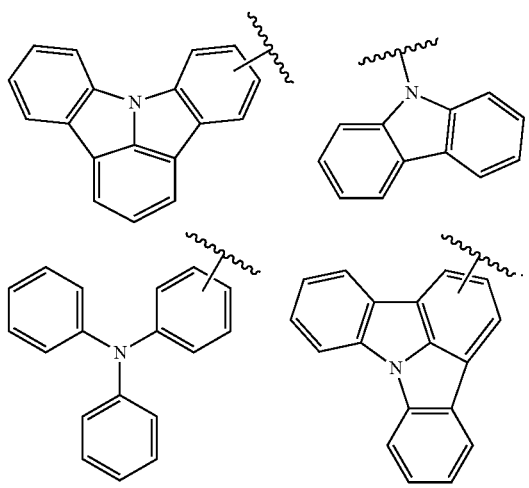

[Formula 3]

12. The organic light emitting diode according to claim 11, wherein the organic emitting layer includes a hole injection layer (HIL), a hole transporting layer (HTL), an emitting material layer (EML), an electron transporting layer (ETL), and an electron injection layer (EIL), and wherein at least one selected from the group consisting of the HIL, the HTL, the EML, the ETL, and the EIL includes the delayed fluorescence compound.

13. The organic light emitting diode according to claim 11, wherein a difference between a singlet energy of the delayed fluorescence compound and a triplet energy of the delayed fluorescence compound is less than 0.3 eV.

14. The organic light emitting diode according to claim 11, wherein the organic emitting layer further includes a host, and the delayed fluorescence compound is used as a dopant.

15. The organic light emitting diode according to claim 14, wherein a difference between a highest occupied molecular orbital (HOMO) of the host and a HOMO of the dopant or a difference between a lowest unoccupied molecular orbital (LUMO) of the host and a LUMO of the dopant is less than 0.5 eV.

16. The organic light emitting diode according to claim 11, wherein the organic emitting layer further includes a dopant, and the delayed fluorescence compound is used as a host.

17. The organic light emitting diode according to claim 11, wherein the organic emitting layer further includes a host and a first dopant, and the delayed fluorescence compound is used as a second dopant, and wherein a triplet energy of the second dopant is smaller than a triplet energy of the host and larger than a triplet energy of the first dopant.

18. A display device, comprising:
a substrate;
an organic light emitting diode on the substrate and including a first electrode, a second electrode facing the first electrode, and an organic emitting layer between the first electrode and the second electrode, the organic emitting layer including a delayed fluorescence compound;
an encapsulation film on the organic light emitting diode; and
a cover window on the encapsulation film,
wherein the delayed fluorescence compound consists of a first electron donor moiety of indolo-[3,2,1-j,k]carbazole, a second electron donor moiety selected from the group consisting of indolo-[3,2,1-j,k]carbazole, carbazole, and triphenylamine, and an electron acceptor moiety selected from the group consisting of dibenzothiophene sulfone and diphenyl sulfone,
wherein the first and second electron donor moieties are directly attached to the electron acceptor moiety, and the electron acceptor moiety is attached to a third position or a sixth position of the first electron donor moiety.

19. A display device, comprising:
a substrate;
an organic light emitting diode on the substrate and including a first electrode, a second electrode facing the first electrode and an organic emitting layer between the first and second electrodes, the organic emitting layer including a delayed fluorescence compound of Formula 1;
an encapsulation film on the organic light emitting diode; and
a cover window on the encapsulation film,

[Formula 1]

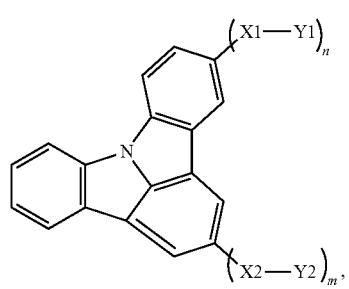

wherein one of m and n is 1, and the other one of m and n is 0, and wherein each of X1 and X2 is independently selected from Formula 2, and each of Y1 and Y2 is independently selected from Formula 3:

[Formula 2]

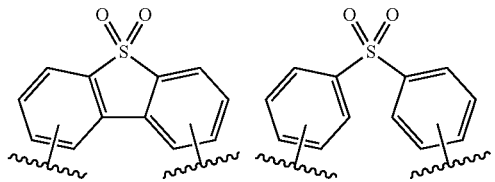

[Formula 3]

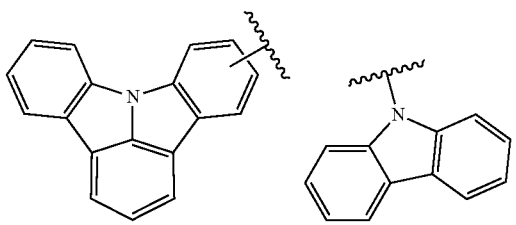

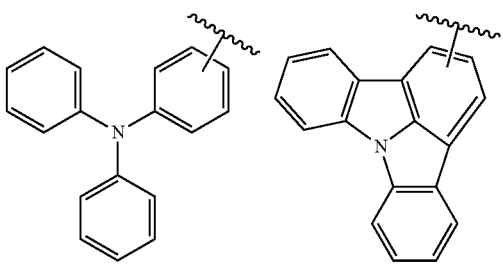

* * * * *